Figure 1A:
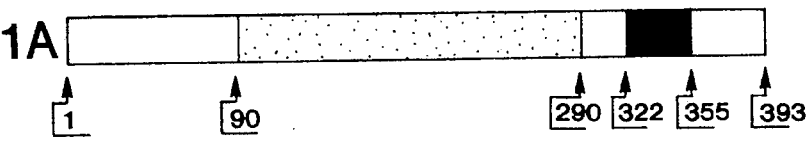

United States Patent [19]

Halazonetis

[11] Patent Number: 5,573,925
[45] Date of Patent: Nov. 12, 1996

[54] P53 PROTEINS WITH ALTERED TETRAMERIZATION DOMAINS

[75] Inventor: Thanos D. Halazonetis, Philadelphia, Pa.

[73] Assignee: The Wistar Institute of Anatomy and Biology, Philadelphia, Pa.

[21] Appl. No.: 347,792

[22] Filed: Nov. 28, 1994

[51] Int. Cl.$^6$ .......................... A61K 31/70; C07H 21/04; C12P 21/04; C07K 19/00

[52] U.S. Cl. ........................ 435/69.7; 536/23.4; 530/350; 514/44

[58] Field of Search ............................ 514/44; 536/23.4; 435/69.7

[56] References Cited

U.S. PATENT DOCUMENTS 5,362,623  11/1994  Vogelstein et al. .......................... 435/6

FOREIGN PATENT DOCUMENTS

| | | |
|---|---|---|
| 2044940 | 12/1992 | Canada . |
| 390323 | 10/1990 | European Pat. Off. . |
| 475623 | 3/1992 | European Pat. Off. . |
| 518650 | 12/1992 | European Pat. Off. . |
| WO93/22430 | 11/1993 | WIPO . |
| WO94/00601 | 1/1994 | WIPO . |
| WO94/06910 | 3/1994 | WIPO . |
| WO94/10308 | 5/1994 | WIPO . |
| WO94/10306 | 5/1994 | WIPO . |
| WO94/12202 | 6/1994 | WIPO . |
| WO94/16716 | 8/1994 | WIPO . |

OTHER PUBLICATIONS

Reed, M. et al. (1993) "p53 domains: suppression, transformation, and transactivation" *Gene Expression* 3(1):95–107.

Sellers, J. W. et al. (1989) "Changing Fos oncoprotein to a Jun-independent DNA-binding protein with GCN4 dimerization specificity by swapping 'leucine zippers'" *Nature* 341:74–76.

Oertel-Buchheit, P. et al. (1993) "Spacing requirements between LexA operator half-sites can be relaxed by fusing the LexA DNA binding domain with some alternative dimerization domains" *J. Mol. Biol.* 229:1–7.

Miller, C. W. et al. (1993) "Mutant p53 proteins have diverse intracellular abilities to oligomerize and activate transcription" *Oncogene* 8:1815–1824.

Iwabuchi, K. et al. (1993) "Use of the two–hybrid system to identify the domain of p53 involved in oligomerization" *Oncogene* 8:1693–1696.

A. Ferre–D'Amare et al, "Recognition by Max of its Cognate DNA Through a Dimeric b/HLH/Z Domain", *Nature*, 363:38–45 (May 6, 1993).

C. Vinson et al, "Scissors–Grip Model for DNA Recognition by a Family of Leucine Zipper Proteins", *Science*, 246:911–916 (Nov. 17, 1989).

S. Alberti et al, "Genetic Analysis of the Leucine Heptad Repeats of Lac Repressor: Evidence for a 4–helical Bundle", *EMBO J.*, 12:3227–3236 (1993).

T. Halazonetis et al, "Conformational Shifts Propagate from the Oligomerization Domain of p53 to its Tetrameric DNA Binding Domain and Restore DNA Binding to Select p53 Mutants", *EMBO J.*, 12(13):5057–5064 (Dec., 1993) [Halazonetis I].

T. Halazonetis et al, "Wild–Type p53 Adopts a 'Mutant'–Like Conformation when Bound to DNA", *EMBO J.*, 12(3):1021–1028 (Mar., 1993) [Halazonetis II].

T. Halazonetis et al, "c–Jun Dimerizes with itself and with c–Fos, Forming Complexes of Different DNA Binding Affinities", *Cell*, 55:917–924 (Dec. 2, 1988) [Halazonetis III].

Y. Wang et al, "p53 Domains: Identification and Characterization of Two Autonomous DNA–Binding Regions", *Genes & Development*, 7:2575–2586 (Dec., 1993) [Wang I].

P. Wang et al, "p53 Domains: Structure, Oligomerization, and Transformation", *Mol. Cell. Biol.*, 14(8):5182–5191 (Aug., 1994) [Wang II].

T. Hupp et al, "Regulation of the Specific DNA Binding Function of p53", *Cell*, 71:875–886 (Nov. 27, 1992) [Hupp I].

T. Hupp et al, "Activation of the Cryptic DNA Binding Function of Mutant Forms of p53", *Nucl. Acids Res.*, 21(14):3167–3174 (Jul. 14, 1993) [Hupp III].

T. Fujiwara et al, "A Retroviral Wild–type p53 Expression Vector Penetrates Human Lung Cancer Spheroids and Inhibits Growth by Inducing Apoptosis", *Cancer Res.*, 53:4129–4133 (Sep. 15, 1993) [Fujiwara I].

T. Fujiwara et al, "Induction of Chemosensitivity in Human Lung Cancer Cells in vivo by Adenovirus–Mediated Transfer of the Wild–Type p53 Gene", *Cancer Res.*, 54:2287–2291 (May 1, 1994) [Fujiwara II].

G. Shaulsky et al, "Nuclear Localization is Essential for the Activity of p53 Protein", *Oncogene*, 6:2056–2065 (Nov., 1991) [Shaulsky I].

G. Shaulsky et al, "Nuclear Accumulation of p53 Protein is Mediated by Several Nuclear Localization Signals and Plays a Role in Tumorigenesis", *Mol. Cell. Biol.*, 10:(12):6565–6577 (Dec., 1990) [Shaulsky II].

(List continued on next page.)

Primary Examiner—Robert A. Wax
Assistant Examiner—Kawai Lau
Attorney, Agent, or Firm—Howson and Howson

[57] ABSTRACT

The present invention provides p53 proteins with altered tetramerization domains that retain wild-type p53 function, and the ability to form tetramers and have at least one of the following characteristics: (1) do not hetero-oligomerize with wild-type p53 or tumor-derived p53 mutants, and (2) restricted DNA binding specificity from an alteration in the way that the tetramerization domain orients the DNA binding domains of a p53 tetramer relative to one another. The invention also provides nucleic acids encoding the above proteins and methods of enhancing the cellular response to DNA damaging agents, treating diseases characterized by abnormal cell proliferation, and inducing immune tolerance to facilitate transplants and treatment of autoimmune disease, by administration of proteins of the invention or nucleic acid sequences encoding the proteins of the invention.

15 Claims, 4 Drawing Sheets

OTHER PUBLICATIONS

J. Oliner et al, "Amplification of a Gene Encoding a p53–Associated Protein in Human Sarcomas", *Nature*, 358:80–83 (Jul. 2, 1992) [Oliner I].

J. Oliner et al, "Oncoprotein MDM2 Conceals the Activation Domain of Tumor Suppressor p53", *Nature*, 362:857–860 (Apr. 29, 1993) [Oliner II].

K. Zhang et al, "Drosophila Homolog of the Mammalian jun Oncogene is Expressed During Embryonic Development and Activates Transcription in Mammalian Cells", *Proc. Natl. Acad. Sci. USA*, 87:6281–6285 (Aug., 1990) [Zhang I].

L. Zhang et al, "Antibody–Promoted Dimerization Bypasses the Regulation of DNA Binding by the Heme Domain of the Yeast Transcriptional Activator HAP1", *Proc. Natl. Acad. Sci. USA*, 90:2851–2855 (Apr., 1993) [Zhang II].

J. Chen et al, "Heterogeneity of Transcriptional Activity of Mutant p53 Proteins and p53 DNA Target Sequences", *Oncogene*, 8:2159–2166 (Aug. 1993) [Chen I].

J. Chen et al, "Mapping of the p53 and mdm–2 Interaction Domains", *Mol. Cell. Biol.*, 13(7):4107–4114 (Jul., 1993) [Chen II].

L. Diller et al, "p53 Functions as a Cell Cycle Control Protein in Osteosarcomas", *Mol. Cell. Biol.*, 10(11):5772–5781 (Nov., 1990).

C. Harris, "p53: At the Crossroads of Molecular Carcinogenesis and Risk Assessment", *Science*, 262:1980–1981 (Dec. 24, 1993).

R. Zakut–Houri et al, "Human p53 Cellular Tumor Antigen: cDNA Sequence and Expression in COS Cells", 'EMBO J., 4(5):1251–1255 (May, 1985).

T. Soussi et al, "Structural Aspects of the p53 Protein in Relation to Gene Evolution", *Oncogene*, 5:945–952 (Jul. 1990).

J. Pietenpol et al, "Sequence–Specific Transcriptional Activation is Essential for Growth Suppression by p53", *Proc. Natl. Acad. Sci. USA*, 91:1998–2002 (Mar., 1994).

S. Kraiss et al, "Oligomerization of Oncoprotein p53", *J. Virol.*, 62(12):4737–4744 (Dec., 1988).

T. Friedmann, "Gene Therapy of Cancer Through Restoration of Tumor–Suppressor Functions", *Cancer Supplement*, 70(6):1810–1817 (Sep. 15, 1992).

P. Friedman et al, "The p53 Protein is an Unusually Shaped Tetramer that Binds Directly to DNA", *Proc. Natl. Acad. Sci. USA*, 90:3319–3323 (Apr., 1993).

P. Hainaut et al, "Analysis of p53 Quaternary Structure in Relation to Sequence–Specific DNA Binding", *Oncogene*, 9:299–303 (Jan., 1994).

W. El–Deiry et al, "WAF1, a Potential Mediator of p53 Tumor Suppression", *Cell*, 75:817–825 (Nov. 19, 1993).

X. Wu et al, "The p53–mdm–2 Autoregulatory Feedback Loop", *Genes & Development*, 7:1126–1132 (Jul., 1993).

M. Kastan et al, "A Mammalian Cell Cycle Checkpoint Pathway Utilizing p53 and GADD45 is Defective in Ataxia–Telangiectasia", *Cell*, 71:587–597 (Nov. 13, 1992).

N. Pavletich et al, "The DNA–Binding Domain of p53 Contains the Four Conserved Regions and the Major Mutation Hot Spots", *Genes & Development*, 7:2556–2564 (Dec., 1993).

S. Fields et al, "Presence of a Potent Transcription Activating Sequence in the p53 Protein", *Science*, 249:1046–1049 (Aug. 31, 1990).

J. Bargonetti et al, "Site–Specific Binding of Wild–Type p53 to Cellular DNA is Inhibited by SV40 T Antigen and Mutant p53", *Genes & Development*, 6:1886–1898 (Oct., 1992).

C. Finlay et al, "The p53 Proto–Oncogene can Act as a Suppressor of Transformation", *Cell*, 57:1083–1093 (Jun. 30, 1989).

D. Eliyahu et al, "Wild–Type p53 can Inhibit Oncogene–Mediated Focus Formation", *Proc. Natl. Acad. Sci. USA*, 86:8763–8767 (Nov., 1989).

S. Baker et al, "Suppression of Human Colorectal Carcinoma Cell Growth by Wild–Type p53", *Science*, 249:912–915 (Aug. 24, 1990).

W. Mercer et al, "Negative Growth Regulation in a Glioblastoma Tumor Cell Line that Conditionally Expresses Human Wild–Type p53", *Proc. Natl. Acad. Sci. USA*, 87:6166–6170 (Aug., 1990).

W. Isaacs et al, "Wild–Type p53 Suppresses Growth of Human Prostate Cancer Cells Containing Mutant p53 Alleles", *Cancer Res.*, 51:4716–4720 (Sep. 1, 1991).

S. Kern et al, "Oncogenic Forms of p53 Inhibit p53–Regulated Gene Expression", *Science*, 256:827–830 (May 8, 1992).

E. Yonish–Rouach et al, "p53–Mediated Cell Death: Relationship to Cell Cycle Control", *Mol. Cell. Biol.*, 13(3):1415–1423 (Mar., 1993).

S. Lowe et al, "p53–Dependent Apoptosis Modulates the Cytotoxicity of Anticancer Agents", *Cell*, 74:957–967 (Sep. 24, 1993).

J. Milner et al, "Contranslation of Activated Mutant p53 with Wild Type Drives the Wild–Type p53 Protein into the Mutant Conformation", *Cell*, 65:765–774 (May 31, 1991).

G. Farmer et al, "Wild–Type p53 Activates Transcription in vitro", *Nature*, 358:83–86 (Jul. 2, 1992).

T. Abel et al, "Action of Leucine Zippers", *Nature*, 341:24–25 (Sep. 7, 1989).

P. Kurokawa et al, "Differential Orientations of the DNA–Binding Domain and Carboxy–Terminal Dimerization Interface Regulate Binding Site Selection by Nuclear Receptor Heterodimers", *Genes & Development*, 7:1423–1435 (Jul., 1993).

R. Marmorstein et al, "DNA Recognition by GAL4: Structure of a Protein–DNA Complex", *Nature*, 356:408–414 (Apr. 2, 1992).

E. O'Shea et al, "Mechanism of Specificity in the Fos–Jun Oncoprotein Heterodimer", *Cell*, 68:699–708 (Feb. 21, 1992).

D. Krylov et al., "A Thermodynamic Scale for Leucine Zipper Stability and Dimerization Specificity: e and g Interhelical Interactions", *EMBO J.*, 13(12):2849–2861 (Jun. 15, 1994).

S. Alberti et al, "Genetic Analysis of the Leucine Heptad Repeats of Lac Repressor: Evidence for a 4–Helical Bundle", *EMBO J.*, 12(8):3227–3236 (Aug., 1993).

P. Harbury et al, "A Switch Between Two–, Three–, and Four–Stranded Coiled Coils in GCN4, Leucine Zipper Mutants", *Science*, 262:1401–1407 (Nov. 26, 1993).

H. Sakamoto et al, "Specific Sequences from the Carboxyl Terminus of Human p53 Gene Product Form Anti–Parallel Tetramers in Solution", *Proc. Natl. Acad. Sci. USA*, 91:8974–8979 (Sep., 1994).

J. Momand et al, "The mdm–2 Oncogene Product Forms and Complex with the p53 Protein and Inhibits p53–Mediated Transactivation", *Cell*, 69:1237–1245 (Jun. 26, 1992).

P. Pellett et al, "Nucleotide Sequence and Predicted Amino Acid Sequence of a Protein Encoded in a Small Herpes Simplex Virus DNA Fragment Capable of Trans–Inducing alpha Genes", *Proc. Natl. Acad. Sci. USA*, 82:5870–5874 (Sep., 1985).

J. Lin et al, "Several Hydrophobic Amino Acids in the p53 Amino–Terminal Domain are Required for Transcriptional Activation, Binding to mdm–2 and the Adenovirus 5 E1B 55–kD Protein", *Genes & Development*, 8:1235–1246 (May, 1994).

L. Cox et al, "Xenopus p53 is Biochemically Similar to the Human Tumour Suppressor Protein p53 and is Induced upon DNA Damage in Somatic Cells", *Oncogene*, 9:2951–2959 (Oct., 1994).

B. Li et al, "Preferential Overexpression of a 172Arg–Leu Mutant p53 in the Mammary Gland of Transgenic Mice Results in Altered Lobuloalveolar Development", *Cell Growth and Differentiation*, 5:711–721 (Jul., 1994).

J. Richardson et al, "Amino Acid Preferences for Specific Locations at the Ends of alph Helices", *Science*, 240:1648–1652 (Jun. 17, 1988).

J. Schreiber et al, "Recombinant Retroviruses Containing Novel Reporter Genes", *Biotechniques*, 14(5):818–823 (May, 1993).

B. Davidson et al, "A Model System for in vivo Gene Transfer into the Central Nervous System Using an Adenoviral Vector", *Nature Genetics*, 3:219–223 (Mar., 1993).

B. Roessler et al, "Adenoviral–Mediated Gene Transfer to Rabbit Synovium in vivo", *J. Clin. Invest.*, 92:1085–1092 (Aug., 1993).

E. Fynan et al, "DNA Vaccines: Protective Immunizations by Parenteral, Mucosal, and Gene–gun Inoculations", *Proc. Natl. Acad. Sci. USA*, 90:11478–11482 (Dec., 1993).

J. Wolff et al, "Conditions Affecting Direct Gene Transfer into Rodent Muscle in vivo", *Biotechniques*, 11(4):474–485 (Oct., 1991).

R. Mulligan et al, "Selection for Animal Cells that Express the *Escherichia coli* Gene Coding for Xanthine–Guanine Phosphoribosyl–transferase", *Proc. Natl. Acad. Sci. USA*, 78:2072–2076 (Apr., 1981).

I. Hope et al, "GCN4, a Eukaryotic Transcriptional Activator Protein, Binds as a Dimer to Target DNA", *EMBO J.*, 6(9):2781–2784 (Sep., 1987).

A. Chumakov et al., "Analysis of p53 Transactivation through High–Affinity Binding Sites", *Oncogene*, 8:3005–3011 (Nov., 1993).

C. Caron de Fromentel et al, "TP53 Tumor Suppressor Gene: A Model for Investigating Human Mutagenesis", *Genes, Chrom. and Cancer*, 4:1–15 (1992).

E. Shaullan et al, "Tight DNA Binding and Oligomerization are Dispensable for the Ability of p53 to Transactivate Target Genes and Suppress Transformation", *EMBO J.*, 12(7):2789–2797 (Jul., 1993).

E. Culotta et al, "p53 Sweeps Through Cancer Research", *Science*, 262:1958–1961 (Dec., 1993).D. Koshland, "Editorial—Molecule of the Year", *Science*, 262:1953 (Dec., 1993).

S. Maheswaran et al, "Physical and Functional Interaction Between WT1 and p53 Proteins", *Proc. Natl. Acad. Sci. USA*, 90:5100–5104 (Jun., 1993).

T. Unger et al, "p53: a Transdominant Regulator of Transcription whose Function is Ablated by Mutations Occurring in Human Cancer", *EMBO J.*, 11(4):1383–1390 (Apr., 1992) [Unger I].

T. Unger et al, "Functional Domains of Wild–Type and Mutant p53 Proteins Involved in Transcriptional Regulation, Transdominant Inhibition, and Transformation Suppression", *Mol. Cell. Biol.*, 13(9):5186–5194 (Sep., 1993) [Unger II].

T. Ellenberger et al, "The GCN4 Basic Region Leucine Zipper Binds DNA as a Dimer of Uninterrupted alpha Helices: Crystal Structure of the Protein-DNA Complex", *Cell*, 71:1223–1237 (Dec., 1992).

Wild-type p53

Heterologous Dimerization Domain Chimeras

Heterologous Tetramerization Domain Chimeras

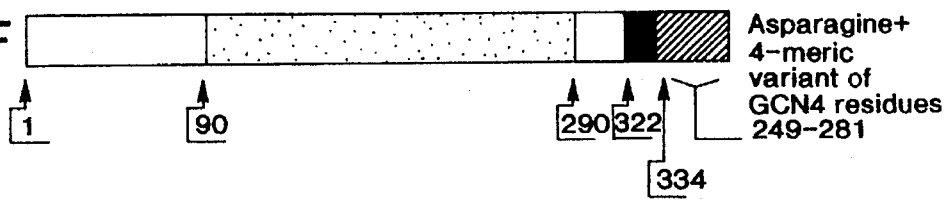

FIG. 1F — Asparagine+ 4-meric variant of GCN4 residues 249-281

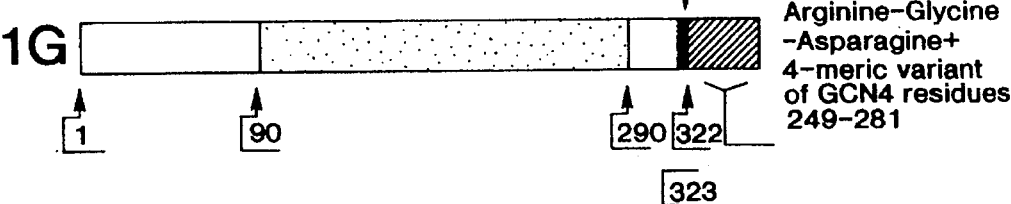

FIG. 1G — Arginine-Glycine-Asparagine+ 4-meric variant of GCN4 residues 249-281

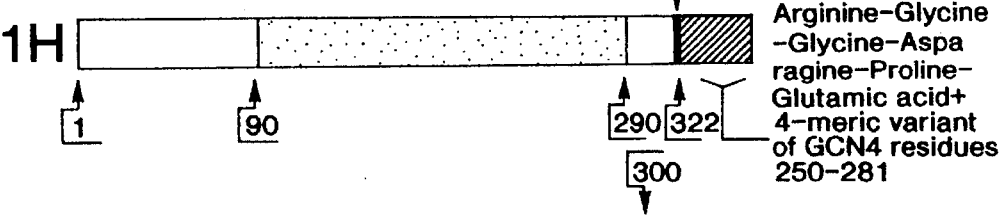

FIG. 1H — Arginine-Glycine-Glycine-Asparagine-Proline-Glutamic acid+ 4-meric variant of GCN4 residues 250-281

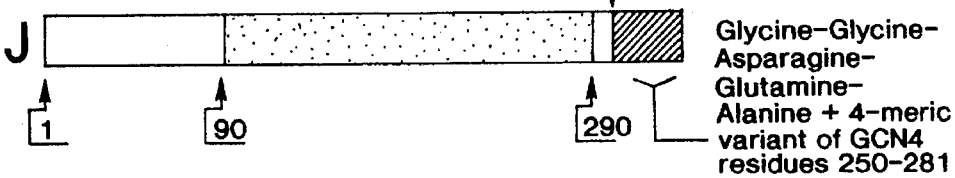

FIG. 1J — Glycine-Glycine-Asparagine-Glutamine-Alanine + 4-meric variant of GCN4 residues 250-281

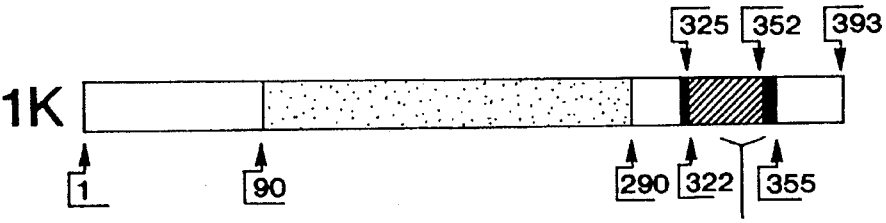

FIG. 1K — Arginine-Glycine-Asparagine+4-meric variant of GCN4 residues 249-281+ Isoleucine

5,573,925

P53 PROTEINS WITH ALTERED TETRAMERIZATION DOMAINS

I. FIELD OF THE INVENTION

The present invention relates to the field of p53 proteins with altered oligomerization domains, polynucleotide sequences encoding them, and their use in therapy.

II. BACKGROUND OF THE INVENTION

Wild-type (wt) p53 is a sequence-specific DNA binding protein found in humans and other mammals, which has tumor suppressor function [See, e.g., Harris (1993), Science, 262:1980–1981]. The wild-type p53 protein functions to regulate cell proliferation and cell death (also known as apoptosis). It also participates in the response of the cell to DNA damaging agents [Harris (1993), cited above]. In more than half of all human tumors p53 is inactivated by mutations and is therefore unable to arrest cell proliferation or induce apoptosis in response to DNA damaging agents, such as radiation and chemotherapeutics commonly used for cancer treatment. The nucleotide and amino acid sequences of human p53 are reported below as SEQ ID NOS: 1 and 2, respectively [Zakut-Houri et al, (1985), EMBO J., 4:1251–1255; GenBank Code Hsp53]. The amino acid sequence of p53 is conserved across evolution [Soussi et al, (1990), Oncogene, 5:945–952], suggesting that its function is also conserved.

At the biochemical level, p53 is a tetrameric DNA sequence-specific transcription factor. Its DNA binding and transcriptional activities are required for p53 to suppress tumor growth [Pietenpol et al, (1994), Proc. Natl. Acad. Sci. USA, 91:1998–2002]. p53 forms homotetramers in the absence of DNA and maintains its tetrameric stoichiometry when bound to DNA [Kraiss et al, (1988), J. Virol., 62:4737–4744; Stenger et al, (1992), Mol. Carcinog., 5:102–106; Sturzbecher et al, (1992), Oncogene, 7:1513–1523; Friedman et al, (1993), Proc. Natl. Acad. Sci. USA, 90:3319–3323; Halazonetis and Kandil (1993), EMBO J., 12:5057–5064; and Hainaut et al, (1994), Oncogene, 9:299–303]. Consistent with the observation that p53 binds DNA as a homotetramer, the known physiologically relevant DNA sites recognized by p53 contain four pentanucleotide repeats [El-DeiryDeiry et al, (1993), Cell, 75:817–825; Wu et al, (1993), Genes Dev., 7:1126–1132; Kastan et al, (1992), Cell, 71:587–597]. Each pentanucleotide repeat is recognized by one subunit of the p53 homotetramer [Halazonetis and Kandil (1993), cited above; Cho et al, (1994), Science, 265:346–355]. The ability of p53 to bind DNA in a sequence-specific manner maps to amino acid residues 90–290 of SEQ ID NO: 2 [Halazonetis and Kandil (1993), cited above; Pavletich et al, (1993), Genes Dev., 7:2556–2564; Wang et al, (1993), Genes Dev., 7:2575–2586].

Once bound to DNA, p53 activates gene transcription from neighboring promoters. The ability of p53 to activate gene transcription has been mapped to within amino acid residues 1–90 of SEQ ID NO: 2 [Fields et al, (1990), Science, 249:1046–1049].

The C-terminus of the human p53 tumor suppressor protein (i.e., amino acids 290–393 of human p53, SEQ ID NO: 2) has two functions. It induces p53 oligomerization and it regulates p53 DNA binding by controlling the conformation of p53 tetramers. These two functions map to independent regions. Oligomerization maps to amino acid residues 322–355 of SEQ ID NO: 2 [Wang et al, (1994), Mol. Cell. Biol., 14:5182–5191; Clore et al, (1994), Science, 265:386–391]. Regulation of DNA binding maps to amino acid residues 364–393 of human p53 [SEQ ID NO: 2] or to the corresponding region encompassing residues 361–390 of mouse p53 [SEQ ID NO: 15] [Hupp et al, (1992), Cell, 71:875–886; Halazonetis et al, (1993), EMBO J., 12:1021–1028; Halazonetis and Kandil (1993), cited above; Genbank locus Mmp53r].

Mutations of the p53 protein in most human tumors involve the sequence-specific DNA binding domain, so that the mutant proteins are unable to bind DNA [Bargonetti et al, (1992), Genes Dev., 6:1886–1898]. The loss of p53 function is critical for tumor development. Introduction of wild-type p53 into tumor cells leads to arrest of cell proliferation or cell death [Finlay et al, (1989), Cell, 57:1083–1093; Eliyahu et al, (1989), Proc. Natl. Acad. Sci. USA, 86:8763–8767; Baker et al, (1990), Science, 249:912–915; Mercer et al, (1990), Proc. Natl. Acad. Sci. USA, 87:6166–6170; Diller et al, (1990), Mol. Cell. Biol., 10:5772–5781; Isaacs et al, (1991), Cancer Res., 51:4716–4720; Yonish-Rouach et al, (1993), Mol. Cell. Biol., 13:1415–1423; Lowe et al, (1993), Cell, 74:957–967; Fujiwara et al, (1993), Cancer Res., 53:4129–4133; Fujiwara et al, (1994), Cancer Res., 54:2287–2291]. Thus, introduction of wild-type p53 into tumor cells has been proposed to be a viable approach to treat human cancer [see, e.g., International Patent Applications WO 9406910 A, WO 9416716 A, WO 9322430 A1, EP 390323, and EP 475623 A1].

However, most tumors express mutant versions of p53 at high levels [Harris (1993), cited above]. Because these p53 mutants have intact oligomerization domains, they form hetero-tetramers with wild-type p53. Such hetero-tetramers are biochemically inactive or characterized by considerably reduced activity compared to wild-type p53 tetramers [Milner and Medcalf (1991), Cell, 65:765–774; Bargonetti et al, (1992), cited above; Farmer et al, (1992), Nature, 358:83–86; Kern et al, (1992), Science, 256:827–830]. Thus, if one were to treat human cancer by introduction of wild-type p53 in tumor cells, the effectiveness of this therapeutic approach would be limited by the presence of mutant p53 in the cancer cells.

Thus, there is a need in the art for the identification of compositions which are not inhibited by endogenous p53, as well as for methods for the uses of such compositions for therapeutic purposes.

III. SUMMARY OF THE INVENTION

The present invention provides novel modified p53 proteins, including preferably chimeric proteins formed by the association of sequences of p53 and sequences of other selected proteins, which novel proteins have desirable functional characteristics.

In one aspect, the present invention provides p53 proteins with altered tetramerization domains characterized by the ability to form tetramers, bind DNA and activate transcription indistinguishably from wild-type p53, but incapable of forming hetero-tetramers with p53 proteins that have an intact tetramerization domain, such as wild-type p53 or tumor-derived p53 mutants. These p53 proteins of the invention are preferably chimeric proteins, characterized by disruption of the native p53 tetramerization domain and insertion of a heterologous oligomerization domain in a way that preserves tetramerization.

In another aspect, the invention provides p53 proteins characterized by restricted DNA binding specificity from an alteration in the way the tetramerization domain orients the DNA binding domains of a p53 tetramer relative to one another. These proteins are characterized by deletion of all or a significant portion of, or disruption of, the region between the DNA binding domain (amino acid residues 90–289 of human p53 of SEQ ID NO: 2) and tetramerization domain (amino acid residues 322–355 of human p53 of SEQ ID NO: 2). This region (spanning residues 290–321 of human p53 of SEQ ID NO: 2) is considered an extension of the p53 tetramerization domain.

In still another aspect, the invention provides p53 proteins with both of the characteristics described above, namely: (1) ability to form tetramers, but inability to hetero-tetramerize with p53 proteins having an intact tetramerization domain, such as wild-type p53 or tumor-derived p53 mutants; (2) restricted DNA binding specificity from an alteration in the way that the tetramerization domain orients the DNA binding domains of a p53 tetramer relative to one another.

In still another aspect, the invention provides further modifications of the p53 proteins provided above. These modifications include: (1) altered transcription activation sequences (amino acid residues 1–90 of human p53 of SEQ ID NO: 2); (2) insertion of one or more nuclear localization signals; and (3) replacement of selected regions of the p53 proteins with homologous regions of non-human p53 protein, as well as conventional modifications such as insertion or deletion or substitution of individual amino acid residues throughout the sequence, and the use of linkers between portions of the chimeric proteins.

Still another aspect of this invention provides p53 proteins having two or more of the above-described modifications.

In yet another aspect, the present invention provides a nucleic acid sequence encoding a protein of the invention. These nucleic acids may be inserted into an appropriate vector for delivery to patients for gene therapy. Alternatively the nucleic acids may be inserted into a vector for in vitro expression of a protein of the invention, which is then introduced into patients.

In a further aspect, the invention provides a method of treating an individual having a condition characterized by abnormal cell proliferation by delivering a protein or, preferably, a nucleic acid sequence, of the invention to the patient.

Other aspects and advantages of the present invention are described further in the following detailed description of the preferred embodiments thereof.

IV. BRIEF DESCRIPTION OF THE DRAWINGS

FIG. 1A schematically illustrates wild-type p53. The amino acid numbering, which is also maintained throughout FIGS. 1A–1K, refers to the residues of human p53 as indicated in SEQ ID NO: 2. The entire length of human p53 is 393 amino acids. Symbols for the DNA binding domain (residues 90–290 of SEQ ID NO: 2) (checkerboard bar) and the oligomerization domain (residues 322–355 of SEQ ID NO: 2) (solid bar) are maintained throughout FIGS. 1A–1K.

Figure 1B:
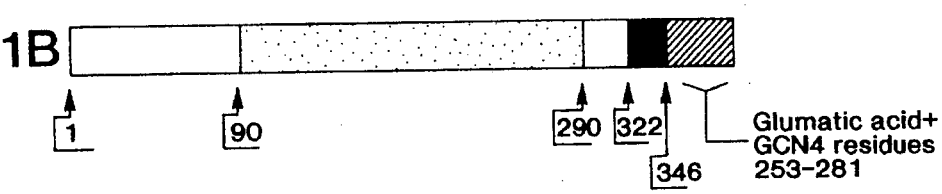

FIG. 1B schematically illustrates a heterologous dimerization domain p53 chimeric protein containing residues 1–346 of p53 [SEQ ID NO: 2], a glutamic acid for cloning convenience and a GCN4 dimerization domain corresponding to residues 253–281 of GCN4 of SEQ ID NO: 4 (hatched bar).

Figure 1C:
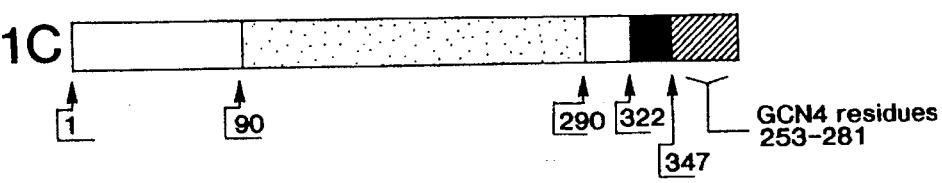

FIG. 1C schematically illustrates a heterologous dimerization domain p53 chimeric protein containing residues 1–347 of p53 [SEQ ID NO: 2] and residues 253–281 of GCN4 of SEQ ID NO: 4 (hatched bar).

Figure 1D:
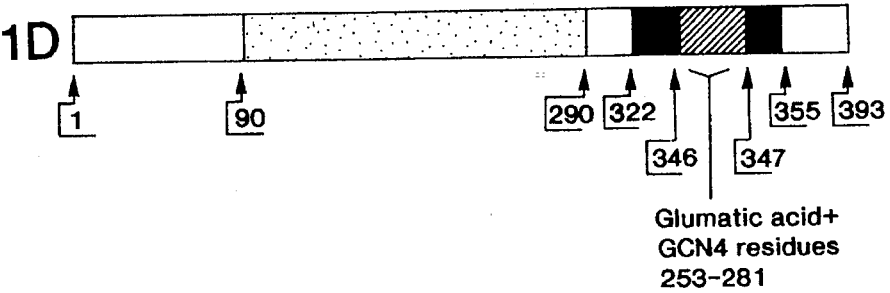

FIG. 1D schematically illustrates a heterologous dimerization domain chimeric p53 protein containing an insertion of a glutamic acid and residues 253–281 of GCN4 of SEQ ID NO: 4 (hatched bar) between residues 346 and 347 of p53 [SEQ ID NO: 2].

Figure 1E:
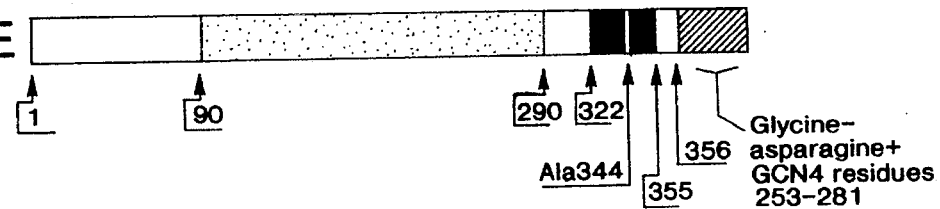

FIG. 1E schematically illustrates a heterologous dimerization domain chimeric p53 protein containing residues 1–356 of human p53 [SEQ ID NO: 2] with a mutation within the native p53 oligomerization domain (leucine 344 to alanine) linked to the dipeptide glycine-asparagine and residues 253–281 of GCN4 of SEQ ID NO: 4 (hatched bar).

FIG. 1F schematically illustrates a heterologous tetramerization domain chimeric p53 protein which contains residues 1–334 of human p53 [SEQ ID NO: 2] linked to an asparagine and then to a tetrameric variant of GCN4 residues 249–281 of SEQ ID NO: 6 (hatched bar).

FIG. 1G schematically illustrates a heterologous tetramerization domain chimeric p53 protein which contains residues 1–325 of human p53 [SEQ ID NO: 2] linked to the tripeptide arginine-glycine-asparagine [SEQ ID NO: 7] and then to a tetrameric variant of GCN4 residues 249–281 of SEQ ID NO: 6 (hatched bar).

FIG. 1H schematically illustrates a heterologous tetramerization domain chimeric p53 protein which contains residues 1–323 of human p53 [SEQ ID NO: 2] linked to the hexapeptide arginine-glycine-glycine-asparagine-proline-glutamic acid [SEQ ID NO: 8] and then to a tetrameric variant of GCN4 residues 250–281 of SEQ ID NO: 6 (hatched bar).

FIG. 1J schematically illustrates a heterologous tetramerization domain chimeric p53 protein which contains residues 1–300 of human p53 [SEQ ID NO: 2] linked to the pentapeptide glycine-glycine-asparagine-glutamine-alanine [SEQ ID NO: 9] and then to a tetrameric variant of GCN4 residues 250–281 of SEQ ID NO: 6 (hatched bar).

FIG. 1K schematically illustrates a heterologous tetramerization domain chimeric p53 protein which contains residues 1–325 of human p53 [SEQ ID NO: 2] linked to the tripeptide arginine-glycine-asparagine [SEQ ID NO: 7], a tetrameric variant of GCN4 residues 249–281 of SEQ ID NO: 6 and an isoleucine (hatched bar), and then followed by residues 352–393 of human p53 [SEQ ID NO: 2].

FIG. 2A schematically illustrates the chimeric p53 protein of FIG. 1F, which serves as a paradigm to indicate the various modifications that can be introduced into any of the p53 proteins of this invention (FIGS. 2B–2F). Symbols for the p53 DNA binding domain (checkerboard bar), the truncated p53 oligomerization domain (solid bar) and the heterologous tetramerization domain (hatched bar) are maintained in FIGS. 2B–2F. Also, the numbering throughout FIGS. 2A–2F refers to the residues of human p53 as indicated in SEQ ID NO: 2.

FIG. 2B schematically illustrates a deletion of residues 300–327 of human p53 [SEQ ID NO: 2], that confers novel DNA binding specificities.

FIG. 2C schematically illustrates the substitution of the transcription activation domain of p53 with that of the herpes simplex virus protein VP16 (reverse hatched bar), also known as α trans-inducing factor.

FIG. 2D schematically illustrates the insertion of a nuclear localization signal (NLS) between amino acid residues 80 and 81 of p53 [SEQ ID NO: 2] (horizontal lined bar). The abbreviation a.a. represents amino acids.

FIG. 2E schematically illustrates the substitution of human p53 residues 3–80 of SEQ ID NO: 2 with the corresponding xenopus sequences (cross-hatched bar).

FIG. 2F schematically illustrates two mutations that enhance function of the p53 proteins [SEQ ID NO: 2] of this invention, such as substitution of Arg 174 with Gln, or Arg 175 with Leu.

Figure 3A:
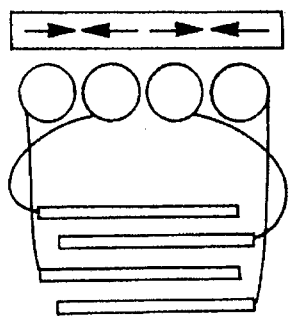

FIG. 3A schematically illustrates a wild-type p53 tetramer bound to a DNA site containing four contiguous pentanucleotides repeats. For FIGS. 3A–3H, the p53 DNA binding domains are shown as circles, the oligomerization domain as a thin rectangle, the linker between the DNA binding and oligomerization domains as curved lines, the DNA as a thick rectangle and the specific pentanucleotides as arrows.

Figure 3B:
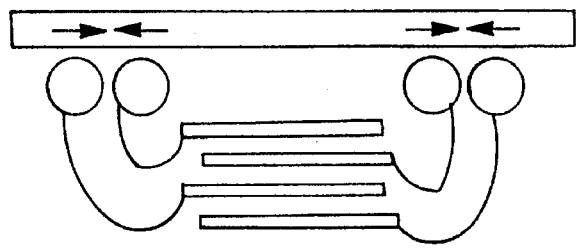

FIG. 3B schematically illustrates a wild-type p53 tetramer bound to a DNA site containing two pentanucleotide pairs separated by a 20–30 nucleotide insert.

Figure 3C:
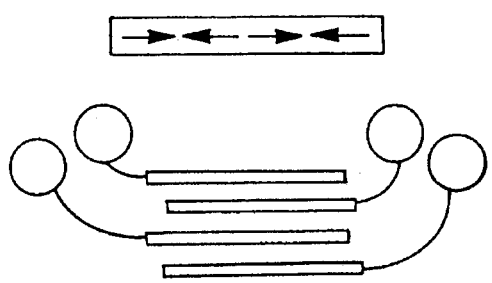
Figure 3D:
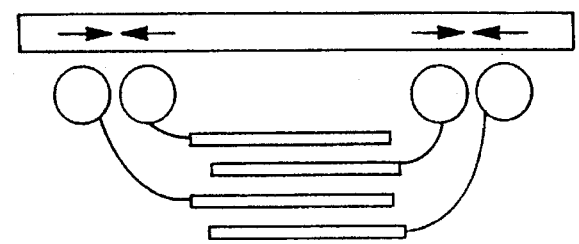

FIGS. 3C and 3D schematically illustrate a p53 tetramer with antiparallel alignment of its oligomerization domains and a short linker between the DNA binding and oligomerization domains. Such a p53 tetramer cannot bind to a DNA site containing four contiguous pentanucleotides repeats (FIG. 3C), but can bind to a DNA site containing two pentanucleotide pairs separated by a 20–30 nucleotide insert (FIG. 3D).

Figure 3E:
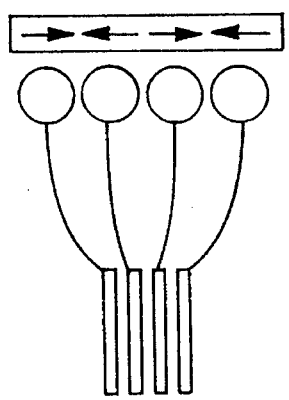

FIG. 3E schematically illustrates a chimeric p53 tetramer with parallel alignment of its oligomerization domains bound to a DNA site containing four contiguous pentanucleotides repeats.

Figure 3F:
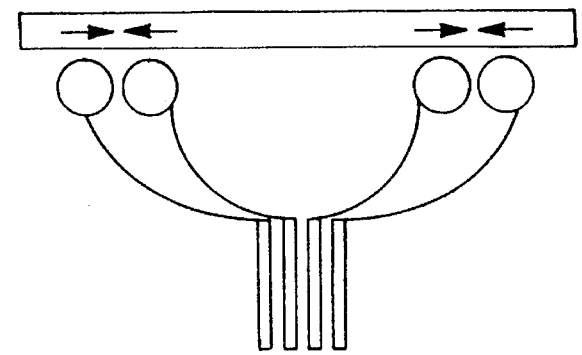

FIG. 3F schematically illustrates a chimeric p53 tetramer with parallel alignment of its oligomerization domains bound to a DNA site containing two pentanucleotide pairs separated by a 20–30 nucleotide insert.

Figure 3G:
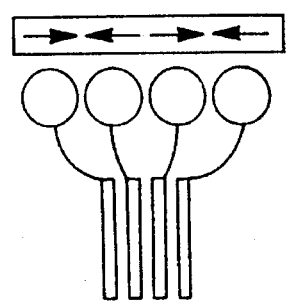
Figure 3H:
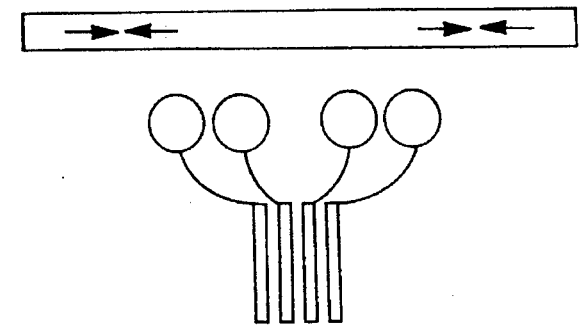

FIGS. 3G and 3H schematically illustrate a chimeric p53 tetramer with parallel alignment of its oligomerization domains and a short linker between the DNA binding and oligomerization domains. Such a p53 tetramer can bind to a DNA site containing four contiguous pentanucleotides repeats (FIG. 3G), but not to a DNA site containing two pentanucleotide pairs separated by a 20–30 nucleotide insert (FIG. 3H).

V. DETAILED DESCRIPTION OF THE INVENTION

The present invention provides p53 proteins with modifications in the native p53 sequence. These modifications, which do not interfere with its native tumor-suppressor function, provide the protein with at least one of the following functional characteristics: (1) the ability to bind DNA and activate transcription like wild-type p53, but to not hetero-oligomerize with wild-type p53 or tumor-derived p53 mutants; and (2) restricted DNA binding specificity from an alteration in the way that the tetramerization domain orients the DNA binding domains of a p53 tetramer relative to one another. In addition nucleic acids encoding such proteins and methods of using such proteins or nucleic acid sequences therapeutically are provided. All references to human p53 residue numbers refer to the numbering scheme provided by Zakut-Houri et al, (1985) [cited above]. The nucleotide and amino acid sequences of human p53 are reproduced as SEQ ID NOS: 1 and 2, respectively.

A. p53 Proteins with Altered Tetramerization Domains

Definitions: A dimerization domain is defined as a domain that allows formation of dimers, while a tetramerization domain is defined as a domain that allows formation of tetramers. An oligomerization domain allows formation of oligomers, which can be of any subunit stoichiometry (of course greater than one). Thus, the term oligomerization domain is more general and encompasses both dimerization and tetramerization domains (which direct formation of oligomers of subunit stoichiometries 2 and 4, respectively).

The term chimeric protein refers to a protein containing sequences from two different proteins, for example from p53 and GCN4.

A1. p53 Associated with a Heterologous Dimerization Domain

In one embodiment, a protein of this invention is comprised of a p53 protein bearing a partial functional inactivation of its tetramerization domain and a heterologous dimerization domain. Thus, certain regions of the p53 tetramerization domain must be maintained (so that the chimeric protein can form tetramers, in spite of containing a heterologous dimerization domain), while other regions are inactivated (so that tetramerization is dependent on the heterologous dimerization domain). The p53 tetramerization domain maps to residues 322–355 of SEQ ID NO: 2 [Wang et al, (1994), cited above; Clore et al, (1994), cited above]. According to this invention, a disruption of the p53 tetramerization domain, involving residues 335–348 of SEQ ID NO: 2 or a subset of these residues, sufficiently disrupts the function of this domain, so that it can no longer drive tetramerization with wild-type p53 or tumor-derived p53 mutants. At the same time, however, introduction of a heterologous dimerization domain reestablishes the ability to form tetramers, which is mediated both by the heterologous dimerization domain and by the residual tetramerization domain of p53.

A heterologous dimerization domain is defined herein as a sequence of amino acids heterologous to p53 and capable of forming homodimers. One example of a dimerization domain is the leucine zipper (LZ) element. A leucine zipper has been defined as stretch of about 35 amino acids containing 4–5 leucine residues separated from each other by six amino acids [Maniatis and Abel (1989), Nature, 341:24–25]. The leucine zipper occurs in a variety of eukaryotic DNA binding proteins, such as GCN4, C/EBP, c-Fos, c-Jun, c-Myc and c-Max.

Heterologous dimerization domains may also be selected from other proteins, such as the retinoic acid receptor, the thyroid hormone receptor or other nuclear hormone receptors [Kurokawa et al, (1993), Genes Dev., 7:1423–1435] or from the yeast transcription factors Gal4 and HAP1 [Marmonstein et al, (1992), Nature, 356:408–414; Zhang et al, (1993), Proc. Natl. Acad. Sci. USA, 90:2851–2855]. One of skill in the art may identify additional suitable dimerization domains, including artificial dimerization domains [O'Shea et al, (1992), Cell, 68:699–708; Krylov et al, (1994), EMBO J., 13:2849–2861]. For ease in description, the leucine zipper of the yeast transcription factor GCN4 is used herein as the exemplary dimerization domain. The nucleotide and amino acid sequences of GCN4 are presented as SEQ ID NO: 3 and NO: 4, respectively. The numbering of the GCN4 nucleotide and amino acid residues follows Hinnenbusch (1984) Proc. Natl. Acad. Sci. USA, 81:6442–6446 and Ellenberger et al, (1992) Cell, 71:1223–1237, respectively. The coding region of GCN4 is encompassed by nucleotide 778–1623 of SEQ ID NO: 3. The nucleotide and amino acid sequence are found in GenBank under the Code Yscgcn4.

Partial functional inactivation of the p53 tetramerization domain can be accomplished by deletions, insertions and/or amino acid substitutions targeting part of this domain. Such mutations should involve residues 335–348 of SEQ ID NO: 2 or a subset of these residues, but need not be confined within the p53 tetramerization domain. For example, a deletion whose N-terminal boundary is within residues 335–348 of SEQ ID NO: 2 may extend as far as the p53 C-terminus. The precise boundaries of the mutations will depend on the nature of the heterologous dimerization domain and the presence, if any, of amino acid sequences introduced for cloning or other purposes between p53 and the heterologous dimerization domain. For example, in one preferred embodiment, residues 1–346 of human p53 [SEQ ID NO: 2] are juxtaposed to the dimerization domain of GCN4 (residues 253–281 of GCN4 SEQ ID NO: 4) through a glutamic acid linker (FIG. 1B). In another embodiment residues 1–347 of human p53 [SEQ ID NO: 2] are juxtaposed to residues 253–281 of GCN4 [SEQ ID NO: 4] (FIG. 1C).

Alternatively, the function of the p53 tetramerization domain may be partially disrupted by insertion of the heterologous dimerization domain within the p53 tetramerization domain and preferably between residues 335 and 348 of human p53 [SEQ ID NO: 2]. In a preferred embodiment (FIG. 1D) a glutamic acid and residues 253–281 of GCN4 [SEQ ID NO: 4] are inserted between residues 346 and 347 of human p53 [SEQ ID NO:2]. Alternatively, the function of the p53 tetramerization domain may be partially disrupted by insertions, deletions or amino acid substitutions, while the heterologous dimerization domain is inserted outside the boundaries of the p53 tetramerization domain. The mutations should again target residues 335–348 of human p53 [SEQ ID NO: 2], or a subset thereof. In one embodiment, the function of the p53 [SEQ ID NO: 2] tetramerization domain is inactivated by substitution of residue 344 by alanine. This mutation only partially disrupts the function of the p53 tetramerization domain (see Examples section). A heterologous dimerization domain can then be inserted even outside the p53 tetramerization domain, for example following residue 356 of human p53 [SEQ ID NO: 2], to reestablish tetramer formation (FIG. 1E).

At least two novel features characterize the class of proteins described here. First these chimeric proteins form tetramers. This was unexpected because the disruption in the p53 tetramerization domain is of sufficient magnitude to disrupt p53 tetramers into monomers. Yet, when the heterologous dimerization domain is introduced, the chimeric protein forms tetramers, rather than dimers, as would be expected. A second novel feature of these chimeric proteins is that their ability to form tetramers with wild-type p53 or with tumor-derived p53 mutants is greatly reduced. This is surprising, because these proteins must utilize p53 structural determinants to form tetramers (recall that in the invention a heterologous dimerization domain is juxtaposed to the p53 sequence). For example the chimeric protein of FIG. 1B that retains residues 1–346 of human p53 [SEQ ID NO: 2], retains all the critical residues (Gly 334, Arg 337, Phe 341 and Leu 344 of SEQ ID NO:2) that are required to make the inter-subunit contacts for tetramer formation (see Example 3 and Clore et al, (1994), cited above). Yet this chimeric protein fails to form tetramers with wild-type p53 or tumor-derived p53 mutants.

The specific embodiments described in this section display the desired functional characteristics, namely of forming tetramers, binding DNA and activating transcription equivalently to wild-type p53, and in addition fail to associate or associate very weakly with tumor-derived p53 mutants (see Examples section). Additional examples of p53 proteins of this invention may be generated by one of skill in the art given the teachings contained herein.

A2. p53 Associated with a Heterologous Tetramerization Domain

In this embodiment of the invention, the p53 protein bears a partial or preferably a complete functional inactivation of its tetramerization domain and contains a heterologous tetramerization domain.

A heterologous tetramerization domain is defined as a sequence of amino acids heterologous to p53 and capable of forming stable homo-tetramers. Exemplary suitable tetramerization domains include that of the lac repressor, or an artificial tetramerization domain, such as variants of the GCN4 leucine zipper that form tetramers [Alberti et al, (1993), EMBO J., 12:3227–3236; Harbury et al, (1993), Science, 262:1401–1407; Krylov et al, (1994), cited above]. One of skill in the art could readily select alternate tetramerization domains. For ease in description, the tetrameric variant of the GCN4 leucine zipper [Harbury et al, (1993), cited above] is used herein as the exemplary tetramerization domain. This variant has isoleucines at positions d of the coiled coil and leucines at positions a, in contrast to the original zipper which has leucines and valines, respectively [Harbury et al, (1993), cited above]. The nucleotide and amino acid sequences of this tetrameric leucine zipper variant are presented in the context of the full-length sequences, as SEQ ID NO: 5 and NO: 6, respectively. The numbering of the amino acid residues follows Ellenberger et al, (1992) [cited above].

The insertion of the tetramerization domain in the p53 chimeric protein can be quite liberal, provided the functions of the transcription activation (also known as transactivation) and DNA binding domains are not disrupted. Preferably, the heterologous tetramerization domain would be inserted C-terminally to residue 290 of human p53 [SEQ ID NO: 2], since this maintains the integrity of both the transactivation and DNA binding domains. Functional inactivation of the p53 tetramerization domain can be accomplished by deletions, insertions and/or amino acid substitutions. Such mutations should involve residues 322–355 of SEQ ID NO: 2, or a subset of these residues, since the p53 tetramerization domain maps to these residues [Wang et al, (1994), cited above; Clore et al, (1994), cited above]. Desirably, selected mutations target residues 328–348 of human p53 [SEQ ID NO: 2], or a subset thereof. Within this region the most critical residues for tetramer formation are residues 337, 341 and 344 of SEQ ID NO: 2. However, mutation of other residues within the regions indicated above can disrupt tetramer formation. While the mutations should involve residues 322–355 [SEQ ID NO: 2], or a subset thereof, they need not be confined within the p53 tetramerization domain. Thus, they can extend as far N-terminally as residue 290 of human p53 [SEQ ID NO: 2] or as far as the p53 C-terminus (residue 393 of SEQ ID NO: 2). In addition to the types of mutations just described, functional inactivation of the p53 tetramerization domain can be accomplished by inserting the heterologous tetramerization domain within residues 322–355 of human p53 [SEQ ID NO: 2], and preferably within residues 328–348 of SEQ ID NO: 2.

Embodiments of the invention are presented in FIGS. 1F–1K. In one embodiment, the chimeric protein comprises a p53 sequence spanning amino acids 1 to 334 of human p53 [SEQ ID NO:2] fused to an asparagine linker and then to a tetrameric variant of GCN4 residues 249–281 [SEQ ID NO:6] (FIG. 1F). In another embodiment, the chimeric protein comprises a p53 sequence spanning amino acids 1 to 325 of human p53 [SEQ ID NO:2] fused to an arginine-glycine-asparagine linker [SEQ ID NO: 7] and then to a tetrameric variant of GCN4 residues 249–281 [SEQ ID NO:6] (FIG. 1G). In another embodiment, the chimeric protein comprises a p53 sequence spanning amino acids 1 to 323 of human p53 [SEQ ID NO:2] fused to an arginine-glycine-glycine-asparagine-proline-glutamic acid linker [SEQ ID NO: 8] and then to a tetrameric variant of GCN4 residues 250–281 [SEQ ID NO:6] (FIG. 1H). In yet another embodiment the chimeric protein comprises a p53 sequence spanning from amino acid 1 to 300 of human p53 [SEQ ID NO:2] fused to a glycine-glycine-asparagine-glutamine-alanine linker [SEQ ID NO: 9] and then to a tetrameric variant of GCN4 residues 250–281 [SEQ ID NO:6] (FIG. 1J). In another embodiment, the chimeric protein comprises a p53 sequence spanning amino acids 1 to 325 of human p53 [SEQ ID NO:2] fused to an arginine-glycine-asparagine linker [SEQ ID NO: 7], a tetrameric variant of GCN4 residues 249–281 [SEQ ID NO:6], an isoleucine linker and then to residues 352–393 of human p53 [SEQ ID NO:2] (FIG. 1K).

One might have expected that a heterologous tetramerization domain would not be able to substitute for the native p53 tetramerization domain, because the function of the tetramerization domain is not only to drive tetramerization, but also to position the subunits appropriately relative to one another, so that the p53 tetramer can align to the DNA site. More specifically, the tetrameric variant of the GCN4 leucine zipper would be expected to be a particularly unsuitable choice for a heterologous tetramerization domain, since it drives parallel subunit assembly [Harbury et al, (1993), cited above], while the native p53 tetramerization domain drives antiparallel assembly [Clore et al, (1994), cited above; Sakamoto et al, (1994), Proc. Natl. Acad. Sci. USA, 91:8974–8978]. Nevertheless, the inventor observed that such chimeric proteins bound DNA as homotetramers with very high efficiency. Without wishing to be bound by theory, the inventor believes that while p53 subunits align antiparallel in the absence of DNA, they adopt a parallel orientation upon DNA binding. Thus a heterologous tetramerization domain that drives parallel assembly of p53 subunits, such as the tetrameric variant of the GCN4 leucine zipper, is compatible with DNA binding.

Because the proteins described in this section form homotetramers and maintain high affinity for the specific p53 DNA sites, but do not maintain the integrity of the native p53 oligomerization domain, they do not form heterotetramers with wild-type p53 or tumor-derived p53 mutants, and thus will display tumor suppressing activity even in cancer cells expressing high amounts of mutant p53. Additional p53 proteins of this invention can be generated by one of skill in the art following the teachings herein.

B. Modifications of p53 Proteins with Altered Tetramerization Domains

In yet another embodiment, the p53 proteins described herein contain modifications. These modifications can be trivial (defined as having no effect on function) or beneficial (i.e. they improve upon some aspect of the protein), and can include deletions, insertions, amino acid substitutions and/or replacement of functional domains or regions of functional domains by functionally equivalent domains or regions of other proteins. Various modifications of the p53 proteins encompassed by the invention are illustrated in FIGS. 2A through 2F. It is understood that the proteins of the invention may contain more than one of the modifications described below.

B1. Length of Sequence between the DNA Binding and Tetramerization Domains

The following modification may be made in the context of wild-type p53 or in the context of the p53 proteins described in sections V.A1 and V.A2 above. This modification restricts the DNA binding specificities of the above mentioned proteins and involves a change in the length of the sequence between the p53 DNA binding and tetramerization domains. This modification does not affect the ability of p53 to tetramerize, rather it affects the positioning of the DNA binding domains relative to one another in a p53 tetramer. Since the function of an oligomerization domain in general is not only to induce oligomerization, but also to bring together the subunits in an appropriate orientation, this modification is considered an alteration of the p53 tetramerization domain, as it affects a function of the tetramerization domain and involves sequences that are extensions of the p53 tetramerization domain.

Changing the length of the sequences between the DNA binding and tetramerization domains can affect the DNA binding properties of wild-type p53 or of a chimeric p53 protein of this invention both in terms of sequence specificity and affinity for DNA. Such changes can therefore confer desired properties.

Without wishing to be bound by theory, the inventor realizes that the tetramerization domain of p53 is the site at which four p53 subunits contact each other. Thus, the positioning of the four p53 DNA binding domains relative to each other is dependent on the length of the sequence between the C-terminal boundary of the DNA binding domain (residue 289 of human p53, [SEQ ID NO: 2]) and the N-terminal boundary of the tetramerization domain (residue 322 for human wild-type p53, [SEQ ID NO:2]). A long linker, such as the linker present in wild-type p53 (i.e., residues 289–322 of SEQ ID NO: 2) provides freedom in positioning the DNA binding domains relative to one another, which in turn allows p53 to bind to different types of DNA sites. A long linker, however, reduces the affinity for DNA, since it allows p53 to adopt multiple conformations, only one of which is compatible with a specific DNA site. A short linker, on the other hand, allows p53 to bind only to specific types of DNA sites, but the affinity for these sites is increased because p53 can adopt few alternate conformations.

The types of DNA sites that wild-type p53 recognizes are exemplified by the sites present in the regulatory sequences of the waf1 and mdm2 genes. The waf1 site contains four contiguous pentanucleotides [El-DeiryDeiry et al, (1993), cited above]. The mdm2 site contains two pairs of contiguous pentanucleotides separated by more than thirty nucleotides [Wu et al, (1993), cited above]. The nucleotide sequences of these two sites are: -GAACA-TGTCC-CAACA-TGTTG- [SEQ ID NO: 10] and -GGTCA-AGTTG-ggacacgtccggcgtcggctgtcggaggagctaagtcc-TGACA-TGTCT- [SEQ ID NO: 11], respectively, with the specific pentanucleotide repeats in capital letters and demarcated by hyphens. Thus, DNA sites recognized by wild-type p53 can have any number of nucleotides between 0 to about 35 separating two pairs of specific contiguous pentanucleotides.

To illustrate the effect of changing the length of the sequence between the p53 DNA binding and tetramerization domains on DNA binding specificity, FIGS. 3A–3H illustrate the effect of deletions between these two domains. FIG. 3A shows a cartoon of a wild-type p53 tetramer bound to a DNA site with contiguous pentanucleotides. FIG. 3B shows the same p53 tetramer bound to a DNA site with a 20–30 nucleotide insert between the 2 pentanucleotide pairs. From FIGS. 3A and 3B it is apparent that the naturally-occurring sequence between the tetramerization and DNA binding domains provides the flexibility for wild-type p53 to recognize both types of DNA sites. In FIGS. 3C and 3D the sequences (linkers) between the tetramerization and DNA binding domains are shortened. This is performed by deletions within the region spanning residues 290–327 of human p53 [SEQ ID NO: 2], preferably involving more than 22 amino acids. Such deletions in the context of wild-type p53 limit the ability to position one pair of DNA binding domains close enough to the other pair. Therefore, DNA sites with contiguous pentanucleotides cannot be recognized (FIG. 3C). However, the same deletions do not limit the ability to recognize DNA sites with a 20–30 nucleotide insert between the two pentanucleotide pairs (FIG. 3D). For example, wild-type p53, and p53 mutants lacking residues 290–297 of SEQ ID NO: 2 or 300–308 of SEQ ID NO: 2 or 300–317 of SEQ ID NO: 2 or 300–321 of SEQ ID NO: 2 bind to both types of DNA sites. But p53 mutants lacking residues 300–327 of SEQ ID NO: 2 or residues 290–297 of SEQ ID NO: 2 and 300–321 of SEQ ID NO: 2 bind only to DNA sites with a 20 nucleotide insert (see Example 3E).

This type of modification achieves the same result as described above for wild-type p53 when the modification is made to the chimeric p53 proteins that retain the antiparallel subunit alignment of wild-type p53. Chimeric p53 proteins that contain a heterologous dimerization domain (Section V.A1 above) have their subunits aligned antiparallel.

Modifications of the p53 chimeric proteins containing a tetramerization domain driving parallel subunit alignment, such as the p53 proteins containing the exemplary tetrameric variant of the GCN4 leucine zipper (Section V.A2 above) produce a different effect. A cartoon of the chimeric protein of FIG. 1F binding to DNA sites of different types is shown in FIGS. 3E and 3F. This chimeric protein can bind to both types of DNA sites via flexibility in positioning its DNA binding domains. Deletions within the sequences between the DNA binding and tetramerization domains create the opposite effect than the one observed for wild-type p53. A short linker, preferably by the deletion of 22 or more amino acids between residues 290 and 334 of SEQ ID NO: 2, allows p53 chimeras with parallel tetramerization domains to recognize only the DNA sites with contiguous pentanucleotides (FIGS. 3G and 3H).

While the effect of changing the length of the sequences between the DNA binding and tetramerization domains was illustrated by introducing deletions between these domains, changes in the length can also be introduced by insertions. The inserted sequences are p53 or non-p53 sequences. It is most meaningful to introduce insertions in the context of p53 proteins of this invention with very short sequences (i.e., 0 to about 12 amino acid residues) between the DNA binding and tetramerization domains, for example the protein of FIG. 1J, to expand the range of DNA sites they can recognize. Finally the length of the sequences between the DNA binding and tetramerization domains can be altered by changing the site of insertion of the heterologous oligomerization domain.

The novelty of this type of modification relates both to the realization that wild-type p53 recognizes DNA sites with 20 or more nucleotides between the two pairs of contiguous pentanucleotides, as well as to the observation that changes in the length of the sequences between the p53 DNA binding and tetramerization domains of p53 modulate its ability to bind to the different types of DNA sites. It has not been appreciated before that wild-type p53 can bind DNA sites, where the pairs of contiguous pentanucleotide repeats are separated by as many as 20 or more nucleotides. While it had been established that wild-type p53 can bind to the mdm2 site, it was thought that this site actually contains two DNA sites (each comprising four contiguous pentanucleotides), as indicated below [Wu et al, (1993), cited above]: -GGTCA-AGTTG-GGACA-CGTCC-ggcgtcggctgtcggag-GAGCTA-AGTCC-TGACA-TGTCT- [SEQ ID NO: 11]. The repeats are indicated by capital letters and are separated by hyphens. However, the underlined repeats contain mismatches from the DNA sites recognized by wild-type p53. Such mismatches, even in the context of an otherwise optimal DNA site, completely abrogate DNA binding [Halazonetis et al, (1993), cited above; and the inventor's own additional unpublished observations]. Furthermore, one of the underlined repeats is not even five nucleotides long. In addition, if p53 could recognize the underlined repeats, then two p53 tetramers should be able to bind to the DNA fragment illustrated above, but the inventor has determined experimentally that only one p53 tetramer can bind. Thus, only the non-underlined repeats are recognized by wild-type p53 in the above DNA fragment, and they are separated by more than 30 nucleotides. See the Examples, which also demonstrate that wild-type p53 can bind DNA sites with more than 20 nucleotides between the pairs of pentanucleotide repeats.

The therapeutic significance of altering the DNA binding properties of the p53 chimeric proteins, or of wild-type p53, relates to the biological consequences of activation of the different p53 target genes. More specifically, induction of the waf1 gene leads to tumor suppression [El-DeiryDeiry et al, (1993), cited above], and is thus desirable for cancer therapy. On the other hand, induction of the mdm2 gene leads to expression of the Mdm2 protein, which in turn downregulates the activity of p53 by masking its transactivation domain [Oliner et al, (1992), Nature, 358:80–83; Momand et al, (1992), Cell, 69:1237–1245; Oliner et al, (1993), Nature, 362:857–860; Wu et al, (1993), cited above], and is thus undesirable for cancer therapy. Introducing appropriate changes in the lengths of the sequences between the DNA binding and tetramerization domains of wild-type p53 or chimeric p53 proteins of the invention, as described above, permits restriction of their DNA binding specificity.

Thus, p53 proteins of this invention are constructed as described above that recognize only DNA sites with contiguous pentanucleotides or only DNA sites with 20 to 30 nucleotide inserts between the two pentanucleotide pairs. Such a p53 protein of this invention that recognizes the waf1 DNA site, but not the mdm2 DNA site, has the ability to suppress tumor growth, but is not subject to negative regulatory feedback by Mdm2. One exemplary p53 protein bearing a modification in the length of the sequences between the DNA binding and tetramerization domains is shown in FIG. 2B, i.e., deletion of residues 300–327 of SEQ ID NO: 2.

B2. Substitutions of Functional Domains or Regions Thereof with Equivalent Domains or Regions of Other Proteins As an example of this type of modification, the p53 transactivation (also known as transcription activation) domain, contained within amino acids 1–90 of human p53 [SEQ ID NO: 2], is substituted with that of another protein, e.g., the herpes simplex virus protein VP16, also known as α trans-inducing factor [Pellett et al, (1985), Proc. Natl. Acad. Sci. USA, 82:5870–5874]. The nucleotide sequence spanning VP16 nucleotides 2074–2307 [Pellett et al, (1985) cited above] is reported as nucleotides 1–234 in SEQ ID NO: 12. The amino acid sequence of the VP16 HSV fragment from amino acid 402 through 479 [Pellett et al, (1985) cited above] is reported as amino acid 1–78 in SEQ ID NO: 13. See, also, GenBank Code Hel1cg.

One exemplary modified p53 protein of the invention is illustrated in FIG. 2C, in which amino acid residues 402–479 of VP16 [aa 1–78 of SEQ ID NO: 13] have replaced amino acid residues 3–80 of human p53 [SEQ ID NO:2]. An equivalent substitution has been reported to maintain p53 tumor suppressor function [Pietenpol et al, (1994), cited above]. The advantage of this substitution is that in certain tumors, overexpression of the Mdm2 protein suppresses p53-mediated transcription by masking its transactivation domain [Oliner et al, (1992), cited above; Momand et al, (1992), cited above; Oliner et al, (1993), cited above]. When the transactivation domain of p53 is replaced by that of VP16, it is no longer inhibited by Mdm2, because Mdm2 does not suppress the transcriptional activity mediated by VP16 [Oliner et al, (1993), cited above].

Substitution of a functional domain can involve part of the domain. For example, amino acid residues 1–52 of p53 [SEQ ID NO: 2] are sufficient to mediate interaction with Mdm2, but residues 18–52 of p53 [SEQ ID NO: 2] are not [Chen et al, (1993), Mol. Cell. Biol., 13:4107–4114]. Thus, replacement of only residues 1–18 of p53 [SEQ ID NO: 2] with sequences from the VP16 activation domain abolishes the p53-Mdm2 interaction. As another example, since within residues 1–52 of p53 [SEQ ID NO: 2], amino acids Leu 14, Phe 19, Leu 22 and Trp 23, are critical for interaction with Mdm2 [Lin et al, (1994), Genes Dev., 8:1235–1246], the substitution involves only these residues.

B3. Nuclear Localization Signals

Nuclear localization is required for p53 function [Shaulsky et al, (1991), Oncogene, 6:2056–2065]. Wild-type p53 contains three nuclear localization signals (NLS), all of which map to the C-terminus of wild-type p53 and specifically to residues 316–325, 369–375 and 379–384 of p53 [SEQ ID NO: 2] [Shaulsky et al, (1990), Mol. Cell. Biol., 10:6565–6577]. Some of the p53 proteins of the invention lack one or more of these NLS. Thus, such proteins have an impaired ability to localize to the nucleus and consequently their function is impaired. It is therefore beneficial to reintroduce NLS. Even p53 proteins that maintain all three NLS may benefit from introduction of additional NLS. Therefore an analog of the p53 proteins described above may contain a NLS fused to its N-terminus, or its C-terminus, or at the junction of the transactivation and DNA binding domains or at the junction of the DNA binding and tetramerization domains or elsewhere in the protein, as long as the function of the p53 protein is not disrupted by insertion of the NLS. FIG. 2D demonstrates the insertion of a NLS at the boundary of the transactivation and DNA binding domains. The NLS may be that of p53 or of any other nuclear protein, such as the NLS of SV40 large T antigen which is comprised of amino acids proline-lysine-lysine-lysine-arginine-lysine-valine [SEQ ID NO: 14] [Kalderon et al, (1984), Cell, 39:499–509]. Additional heterologous NLS are described by Shaulsky et al, (1990); (1991) [cited above].

B4. Substitution by Homologous Non-human p53 Sequences

The amino acid sequence of p53 is conserved across species [Soussi et al, (1990), cited above], implying that function is also conserved. Indeed, analysis of xenopus and human p53 proteins has revealed no functional differences [Cox et al, (1994), Oncogene, 9:2951–2959]. Thus, human p53 sequences of the p53 [SEQ ID NO: 2] proteins of this invention can readily be replaced with the homologous non-human p53 sequences.

The sequences of human p53 [SEQ ID NO: 2] and certain non-human p53 proteins have been aligned by Soussi et al, (1990), cited above. This alignment permits identification of regions that are homologous across species. For p53 species that are not listed by Soussi et al, (1990), cited above, the alignment to the human p53 [SEQ ID NO: 2] sequences is obtained by computer programs commercially available and known in the art, such as the program BESTFIT of the University of Wisconsin GCG package.

The benefit of substituting human p53 [SEQ ID NO: 2] sequences with equivalent non-human sequences relates to the realization that interactions of p53 with specific cellular or viral proteins are species-specific. For example, human p53 is inactivated by the human Mdm2 protein [Oliner et al, (1993), cited above; Momand et al, (1992), cited above; Wu et al, (1993), cited above]. Non-human p53 sequences have lower or no affinity for the human Mdm2. Thus, p53 proteins of this invention that contain non-human p53 sequences are not susceptible to inhibition by Mdm2.

One of skill in the art with resort to the teaching of this invention may readily select which non-human p53 sequence to use, as well as the extent of the region for substitution. For example, the p53-Mdm2 interaction has been mapped to residues 1–52 of p53 [SEQ ID NO: 2], and more specifically to residues 14, 19, 22 and 2of SEQ ID NO: 2 [Chen et al, (1993), cited above; Lin et al, (1994), cited above]. Thus, to eliminate the p53-Mdm2 interaction, N-terminal sequences within residues 1–52 of the p53 proteins of this invention are substituted with the homologous non-human p53 sequences.

The species of p53 that can be used to substitute for the human p53 sequences can readily be selected by one of skill in the art. Species, such as xenopus and trout, that diverge most from human p53 [Soussi et al, (1990), cited above] are preferred, although other species may also be selected.

As an exemplary modification of this type, residues 3–80 of human p53 [SEQ ID NO: 2] are substituted by the homologous xenopus sequence (FIG. 2E) to produce a modified p53 protein incapable of interacting with Mdm2.

B5. Amino Acid Substitutions, Deletions and Insertions

Other modifications of the p53 proteins described in this invention include amino acid substitutions, small deletions and small insertions. (Deletions and insertions within the sequences between the DNA binding and tetramerization domains are discussed in section B1 above.) These modifications involve either the p53 sequences or the heterologous oligomerization domain sequences or both. The modifications may enhance function or introduce a useful property. For example a modification may introduce a tag to optimize protein purification [Scopes (1994), Protein Purification, Principles and Practice, third edition, Springer-Verlag, New York], or may enhance expression and/or stability of a p53 protein of the invention when expressed in vitro or in a patient. Modifications in the p53 fragment may enhance DNA binding and growth suppressing activities. Two such modifications have already been described: substitution of arginine 174 with glutamine or of arginine 175 with leucine (the numbering refers to human p53 [SEQ ID NO: 2]; in mouse p53 the corresponding residues are 171 and 172 of SEQ ID NO: 15, respectively) [Halazonetis and Kandil (1993), cited above; Li et al, (1994), Cell Growth Differentiation, 5:711–721].

Modifications in p53 may also affect interaction with cellular or viral proteins, for example, substitution of leucine 14 of SEQ ID NO: 2 with glutamine and phenylalanine 19 of SEQ ID NO: 2 with serine abolish the p53-Mdm2 interaction [Lin et al, (1994), cited above]. Modifications in the heterologous oligomerization domain may increase the stability of tetramer formation, for example, substitutions that stabilize oligomerization driven by leucine zippers are known [Krylov et al, (1994), cited above; O'Shea et al, (1992), cited above]. As an exemplary modification of this type, residues 174 or 175 of human p53 [SEQ ID NO: 2] are substituted by glutamine or leucine, respectively (FIG. 2F) in a p53 chimeric protein of this invention.

B6. Linkers between p53 and the Heterologous Oligomerization Domain

Another modification of the proteins of this invention is the presence of an amino acid or peptide linker between the p53 fragment and the heterologous oligomerization domain. In one embodiment of this invention (FIG. 1C), there is no linker between p53 and the GCN4 leucine zipper. In other embodiments however (FIGS. 1B, 1F and 1K), there are glutamic acid or asparagine or isoleucine linkers, respectively. Linkers may be present for cloning convenience or to confer some useful property. For example, residues that stabilize specific secondary structure elements, such as α-helices, are known [Richardson and Richardson (1988), Science 240:1648–1652]. Such residues can be introduced in the linkers to stabilize the heterologous oligomerization domains. For example the linkers glycine-asparagine, arginine-glycine-asparagine [SEQ ID NO: 7], arginine-glycine-glycine-asparagine-proline-glutamic acid [SEQ ID NO: 8], glycine-glycine-asparagine-glutamine-alanine [SEQ ID NO: 9] present in the examples shown in FIGS. 1E, 1G and 1K, 1H and 1J, respectively, are all designed to stabilize the N-terminus of the α-helical heterologous oligomerization domain. A variety of other amino acid or peptide linkers may be used for the reasons discussed above, provided they do not interfere with the function of the p53 chimeric protein.

C. Nucleic Acid Sequences Encoding p53 Proteins of the Invention

The present invention further provides nucleic acid sequences encoding the proteins of this invention, which includes the proteins described in sections V.A and V.B above. In addition to the coding strand, the nucleic acid sequences of the invention include the complementary DNA sequence representing the non-coding strand, the messenger RNA sequence, the corresponding cDNA sequence and the RNA sequence complementary to the messenger RNA sequence. Variants of these nucleic acids of the invention include variations due to the degeneracy of the genetic code and are encompassed by this invention. Such variants may be readily identified and/or constructed by one of skill in the art. In certain cases specific codon usage may be employed to optimize expression. The above nucleotide sequences can be included within larger DNA or RNA fragments, or may be interrupted by introns.

In another embodiment the nucleic acids encoding the p53 proteins of the invention are present in the context of vectors suitable for amplification in prokaryotic or eukaryotic cells. Many such vectors are known [Ausubel et al, (1994), cited above] and many of these are commercially available. For example plasmids with bacterial or yeast replication origins allow amplification in bacteria or yeast, respectively. Such vectors allow the production of large quantities of nucleic acids encoding the proteins of the invention, which nucleic acids can be used for gene therapy or for expression of the p53 proteins of the invention.

In yet another embodiment the nucleic acids encoding the proteins of the invention are present in the context of vectors suitable for expression in cell-free extracts or lysates or in prokaryotic or eukaryotic cells. Many such vectors are known [Ausubel et al, (1994), cited above] and many of these are commercially available. For example, the vector pGEM4 (Promega, Madison, Wis.) is suitable for expression of the p53 proteins in cell-free lysates, while the vector pSV2 [Mulligan et al, (1992), cited above] is suitable for expression in mammalian cells. Such vectors allow the production of the proteins of the invention in vitro for analysis of their functional properties or for delivery to patients.

D. Gene Therapy

The nucleic acid sequences of the invention may be inserted into a vector capable of targeting and infecting a desired cell, either in vivo or ex vivo for gene therapy, and causing the encoded p53 protein of this invention to be expressed by that cell. Many such viral vectors are useful for this purpose, e.g., adenoviruses, retroviruses and adeno-associated viruses (AAV) [Schreiber et al, (1993), Biotechniques, 14:818–823; Davidson et al, (1993), Nature Genetics, 3:219–223; Roessler et al, (1993), J. Clin. Invest., 92:1085–1092; Smythe et al, (1994), Ann. Thorac. Surg., 57:1395–1401; Kaplitt et al, (1994), Nature Genetics, 8:148–154]. There has already been success using viral vectors driving expression of wild-type p53 [Fujiwara et al, (1993), Cancer Res., 53:4129–4133; Fujiwara et al, (1994), Cancer Res., 54:2287–2291; Friedmann (1992), Cancer, 70(6 Suppl): 1810–1817; Fujiwara et al, (1994b), Curr. Opin. Oncol., 6:96–105].

For use in gene therapy, these viral vectors containing nucleic acid sequences encoding a p53 protein of the invention, are prepared by one of skill in the art with resort to conventional techniques (see references mentioned above). For example, a recombinant viral vector, e.g. an adenovirus, of the present invention comprises DNA of at least that portion of the viral genome which is capable of infecting the target cells operatively linked to the nucleic acid sequences of the invention. By "infection" is generally meant the process by which a virus transfers genetic material to its host or target cell. Preferably, the virus used in the construction of a vector of the invention is rendered replication-defective to remove the effects of viral replication on the target cells. In such cases, the replication-defective viral genome can be packaged by a helper virus in association with conventional techniques.

Briefly, the vector(s) containing the nucleic acids encoding a protein of the invention is suspended in a pharmaceutically acceptable carrier, such as saline, and administered parenterally (or by other suitable means) in sufficient amounts to infect the desired cells and provide sufficient levels of p53 activity to arrest abnormal cellular proliferation. Other pharmaceutically acceptable carriers are well known to those of skill in the art. A suitable amount of the vector containing the chimeric nucleic acid sequences is between about $10^6$ to $10^9$ infectious particles per mL carrier. The delivery of the vector may be repeated as needed to sustain satisfactory levels of p53 activity, as determined by monitoring clinical symptoms.

As desired, this therapy may be combined with other therapies for the disease or condition being treated. For example, therapy involving the administration of a vector capable of expressing a p53 protein of the invention is well suited for use in conjunction with conventional cancer therapies, including surgery, radiation and chemotherapy.

Nucleic acid sequences driving expression of a p53 protein of the invention may also be introduced by "carriers" other than viral vectors, such as liposomes, nucleic acid-coated gold beads or can simply be injected in situ [Fujiwara et al (1994b), cited above; Fynan et al, (1993), Proc. Natl. Acad. Sci. USA, 90:11478–11482; Cohen (1993), Science, 259:1691–1692; Wolff et al, (1991), Biotechniques, 11:474–485].

E. Pharmaceutical Compositions

The proteins of this invention may also be formulated into pharmaceutical compositions and administered using a therapeutic regimen compatible with the particular formulation. Pharmaceutical compositions within the scope of the present invention include compositions containing a protein of the invention in an effective amount to have the desired physiological effect, e.g. to arrest the growth of cancer cells without causing unacceptable toxicity for the patient.

Suitable formulations for parenteral administration include aqueous solutions of the active compounds in water-soluble or water-dispersible form, e.g. saline. Alternatively, suspensions of the active compounds may be administered in suitable conventional lipophilic carriers or in liposomes.

The compositions may be supplemented by active pharmaceutical ingredients, where desired. Optional antibacterial, antiseptic, and antioxidant agents in the compositions can perform their ordinary functions.

The pharmaceutical compositions of the invention may further contain any of a number of suitable viscosity enhancers, stabilizers, excipients and auxiliaries which facilitate processing of the active compounds into preparations that can be used pharmaceutically. Preferably, these preparations, as well as those preparations discussed below, are designed for parenteral administration. However, compositions designed for oral or rectal administration are also considered to fall within the scope of the present invention.

Those of skill in the pharmaceutical art should be able to derive suitable dosages and schedules of administration. As used herein, the terms "suitable amount" or "effective amount" means an amount which is effective to treat the conditions referred to below. A preferred dose of a pharmaceutical composition containing a protein of this invention is generally effective above about 0.1 mg p53 protein per kg of body weight (mg/kg), and preferably from about 1 mg/kg to about 100 mg/kg. These doses may be administered with a frequency necessary to achieve and maintain satisfactory p53 activity levels. Although a preferred range has been described above, determination of the effective amounts for treatment of each type of tumor or other condition may be determined by those of skill in the art.

Dosage units of such pharmaceutical compositions containing the proteins of this invention preferably contain about 1 mg to 5 g of the protein.

F. Therapeutic Indications

The nucleic acids and proteins of the invention can be introduced into human patients for therapeutic benefits in conditions characterized by insufficient wild-type p53 activity. As stated above, the nucleic acids of the invention may be introduced into the patient in the form of a suitable viral vectors (or by direct DNA delivery) to harness the patient's cellular machinery to express the proteins of the invention in vivo. Alternatively, the proteins of the invention may be introduced into the patient in appropriate pharmaceutical formulations as described above.

As one example, the pharmaceutical compositions of this invention, containing a protein of the invention or a nucleic acid or a viral vector which express a protein of the invention in vivo, may be employed to induce the cellular defence to DNA damaging agents. Examples of DNA damaging agents include sunlight UV irradiation, as well as radiation and chemotherapeutics used for cancer treatment. By administering a suitable amount of a composition of this invention, patients may tolerate higher doses of such DNA damaging agents.

Another therapeutic use of the compositions of this invention is in inducing apoptosis of specific cells, such as proliferating lymphocytes. According to this method of use, a suitable amount of an appropriate pharmaceutical composition of this invention is administered to a subject to enhance the development of immune tolerance. This method may employ both in vivo and ex vivo modes of administration. Preferably, this therapy is useful as the sole treatment or as an accessory treatment to prevent transplant rejection, or to treat autoimmune diseases, e.g., systemic lupus erythrematosis, rheumatoid arthritis and the like.

The pharmaceutical compositions of this invention may also be employed to restore p53 function in tumor cells. Introduction of p53 function in tumor cells leads to arrest of cell proliferation or to cell death [Finlay et al, (1989), cited above; Eliyahu et al, (1989), cited above; Baker et al, (1990), cited above; Mercer et al, (1990), cited above; Diller et al, (1990), cited above; Isaacs et al, (1991), cited above; Yonish-Rouach et al, (1993), cited above; Fujiwara et al, (1993), cited above]. In addition p53 function primes tumor cells to undergo cell death in response to DNA damaging agents currently used in cancer therapy [Lowe et al, (1993), cited above; Fujiwara et al, (1994), cited above; Fisher (1994), Cell, 78:539–542]. Desirably, a suitable amount of the composition of this invention is administered systemically, or locally to the site of the tumor with or without concurrent administration of conventional cancer therapy (i.e. DNA damaging agents).

Additionally, the compositions of this invention may be administered in methods to suppress cell proliferation in diseases other than cancers, which are characterized by aberrant cell proliferation. Among such diseases are included psoriasis, atherosclerosis and arterial restenosis. This method is conducted by administering a suitable amount of the selected composition systemically or locally to the patient.

VI. SPECIFIC EXAMPLES

The present invention provides p53 proteins with modifications in the native p53 sequence. These modifications, which do not interfere with its native tumor-suppressor function, provide the protein with at least one of the following functional characteristics: (1) the ability to bind DNA and activate transcription like wild-type p53, but to not hetero-oligomerize with wild-type p53 or tumor-derived p53 mutants; and (2) restricted DNA binding specificity from an alteration in the way that the tetramerization domain orients the DNA binding domains of a p53 tetramer relative to one another. Exemplary p53 proteins of this invention, which demonstrate the aforementioned functional characteristics, are described in sections V.A and V.B, above. Additional functionally equivalent proteins can be constructed by one of skill in the art with resort to the teachings of sections V.A and V.B and the Examples below.

The following examples illustrate preferred methods for preparing p53 proteins of the invention and characterizing their functional activities. These examples are illustrative only and do not limit the scope of the invention. As throughout the specification, numbering of the human p53 [SEQ ID NO: 2] amino acid residues in the examples follows Zakut-Houri et al, (1994) [cited above], while numbering of the GCN4 residues follows Ellenberger et al, (1992) [cited above].

Example 1—Recombinant Plasmids

Standard cloning procedures were used to prepare the plasmids described below [Ausubel et al, (1994), cited above; Innis et al, (1990), cited above].

A. Plasmid pGEMhump53wt

Plasmid pGEMhump53wt encodes full-length human wild-type p53 [SEQ ID NOS: 1 and 2]. This plasmid was prepared by PCR [Innis et al, (1990), cited above] using a human p53 cDNA, which is readily available to those practicing the art. The PCR procedure was designed to incorporate unique restriction sites within the coding sequence of human p53 [SEQ ID NO: 1]: Kpn I at codon 218, Sst I at codon 299, Sst II at codon 333, Bst BI at codon 338 and Sal I immediately following the termination codon. An Msc I site at codon 138 was eliminated. These changes did not alter the sequence of the encoded p53, and were only performed to expedite construction of mutant proteins bearing altered tetramerization domains or point mutations associated with human cancer. The PCR product of the human p53 cDNA was digested with Nco I and Sal I and cloned in the vector pGEM4 [Promega, Madison, Wis.], which was linearized with Eco RI and Sal I. Synthetic oligonucleotides were used to bridge the Eco RI site of the vector and the Nco I site at the initiation codon of p53. The entire nucleotide sequence of the Eco RI-Sal I human p53 insert in plasmid pGEMhump53wt is presented as SEQ ID NO: 20 (the first nucleotide of the EcoRI site is numbered nucleotide 1). Plasmid, pGEMhump53wt, was used to generate all the p53 mutants described below, as well as for expression of wild-type p53 by in vitro translation.

B. Plasmids of the pGEMhump53 Series Encoding p53 Proteins with Altered Tetramerization Domains

B1. Plasmid pGEMhump53LZ346E

A fragment encoding amino acids 253–281 [SEQ ID NO: 4] of the yeast transcription factor GCN4 [SEQ ID NO: 4] [Hinnenbusch et al, (1984), cited above] was prepared by PCR of plasmid pSP64-GCN4 [Halazonetis et al, (1988), Cell 55:917–924]. The sequence of the 5' PCR primer GCAGAGGAGC AAAAGCTTGA AGACAAGGTT [SEQ ID NO: 21] incorporates a HindIII site, while the sequence of the 3' primer CTTCAGGTCG ACTCAGCGTT CGCCAACTAA TTTC [SEQ ID NO: 2] incorporates a termination codon and a Sal I restriction site. The PCR fragment was blunt-ended at the Hind III site and cloned into pGEMhump53wt linearized with Stu I and Sal I. The resultant plasmid, pGEMhump53LZ346E, encodes amino acids 1–346 of human p53 [SEQ ID NO: 2], a glutamic acid, and then amino acids 253–281 of GCN4 [SEQ ID NO: 4].

B2. Plasmid pGEMhump53LZ347

A fragment encoding amino acids 253–281 [SEQ ID NO: 4] of the yeast transcription factor GCN4 [SEQ ID NO: 4] [Hinnenbusch et al, (1984), cited above] was prepared by PCR of plasmid pSP64-GCN4 [Halazonetis et al, (1988), cited above]. The sequence of the 5' PCR primer ATGAGGCCTT GGAAGACAAG GTTGAAGAAT TG [SEQ ID NO: 23] incorporates a Stu I site, while the sequence of the 3' primer CTTCAGGTCG ACTCAGCGTT CGCCAACTAA TTTC [SEQ ID NO: 22] incorporates a termination codon and a Sal I restriction site. The PCR fragment was cloned into pGEMhump53wt linearized with Stu I and Sal I. The resultant plasmid, pGEMhump53LZ347, encodes amino acids 1–347 of human p53 [SEQ ID NO: 2] and amino acids 253–281 of GCN4 [SEQ ID NO: 4].

B3. Plasmid pGEMhump53LZ335Q

A fragment encoding amino acids 253–281 of the yeast transcription factor GCN4 [SEQ ID NO: 4] [Hinnenbusch et al, (1984), cited above] was prepared by PCR of plasmid pSP64-GCN4 [Halazonetis et al, (1988), cited above]. The sequence of the 5' PCR primer GCAGAGGAGC AAAAGCTTGA AGACAAGGTT [SEQ ID NO: 21] incorporates a Hind III site, while the sequence of the 3' primer CTTCAGGTCG ACTCAGCGTT CGCCAACTAA TTTC [SEQ ID NO: 22] incorporates a termination codon and a Sal I restriction site. The PCR fragment was blunt-ended at the Hind III site and cloned into pGEMhump53wt linearized with Sst II and Sal I. The Sst II site of the vector and the blunt-ended Hind III site of the PCR product were bridged by annealed synthetic oligonucleotides GGGCGTC [SEQ ID NO: 24] and GACGCCCGC [SEQ ID NO: 25]. The resultant plasmid, pGEMhump53LZ335Q, encodes amino acids 1–335 of human p53 [SEQ ID NO: 2], a glutamine, and then amino acids 253–281 of GCN4 [SEQ ID NO: 4].

B4. Plasmid pGEMhump53LZ343

A fragment encoding amino acids 253–281 of the yeast transcription factor GCN4 [SEQ ID NO: 4] [Hinnenbusch et al, (1984), cited above] was prepared by PCR of plasmid pSP64-GCN4 [Halazonetis et al, (1988), cited above]. The sequence of the 5' PCR primer GCAGAGGAGC AAAAGCTTGA AGACAAGGTT [SEQ ID NO: 21] incorporates a Hind III site, while the sequence of the 3' primer CTTCAGGTCG ACTCAGCGTT CGCCAACTAA TTTC [SEQ ID NO: 22] incorporates a termination codon and a Sal I restriction site. The PCR fragment was blunt-ended at the Hind III site and cloned into pGEMhump53wt linearized with Bst BI and Sal I. The Bst BI site of the vector and the blunt-ended Hind III site of the PCR product were bridged by annealed synthetic oligonucleotides CGAAATGTTC CGAGAGCGAA TGAAAC and GTTTCATTCG CTCTCGGAAC ATT [SEQ ID NO: 26 and 27]. The resultant plasmid, pGEMhump53LZ343, encodes amino acids 1–343 of human p53 [SEQ ID NO: 2] and then amino acids 249–281 of GCN4 [SEQ ID NO: 4].

B5. Plasmid pGEMhump53TZ334N

Synthetic oligonucleotides were used to generate a tetrameric variant of the GCN4 leucine zipper. These oligonucleotides TATCCGCGGT AATCGTCTGA AACAGATCGA AGACAAGTTA GAAGAAATCC TTTCGAAGCT CTATCACATC GAG and TTTGTCGACT CAACGTTCAC CCAATAATTT TTTGATGCGC GCTAACTCAT TCTCGATGTG ATAGAGCTTC G [SEQ ID NO: 28 and 29] were subjected to a PCR cycle in the absence of any additional DNA. The PCR product was digested with restriction endonucleases Sst II and Sal I and cloned into pGEMhump53wt linearized with Sst II and Sal I. The resultant plasmid, pGEMhump53TZ334N, encodes amino acids 1–334 of human p53 [SEQ ID NO: 2], an asparagine, and then the tetrameric zipper variant corresponding to amino acids 249–281 [SEQ ID NO: 6] of GCN4.

B6. Plasmid pGEMhump53TZ323RGN

A deletion of residues 324–332 of human p53 [SEQ ID NO: 2] was created within the Sst I–Sst II fragment of plasmid pGEMhump53TZ334N by substituting the wild-type Sst I–Sst II fragment with a PCR fragment generated using the oligonucleotide TTCTCCGCGG AGTGGTTTCT TCTTTGGCTG [SEQ ID NO: 30]. The resultant plasmid, pGEMhump53TZ323RGN, encodes amino acids 1–323 of human p53 [SEQ ID NO: 2], an arginine-glycine-asparagine tripeptide [SEQ ID NO: 7], and then the tetrameric zipper variant corresponding to amino acids 249–281 [SEQ ID NO: 6] of GCN4.

B7. Plasmid pGEMhump53TZ334GNPE

This plasmid is a modification of plasmid pGEMhump53TZ334N. The Sst II-Sal I fragment of pGEMhump53TZ334N containing the tetrameric zipper was modified by PCR using the primer TATCCGCGGT GGAAATCCTG AACTGAAACA GATCGAAGAC AAG [SEQ ID NO: 31]. The PCR fragment was cloned using the Sst II-Sal I sites into pGEMhump53TZ334N, replacing the original Sst II-Sal I fragment. The resultant plasmid, pGEMhump53TZ334GNPE, encodes amino acids 1–334 of human p53 [SEQ ID NO: 2], a glycine-asparagine-proline-glutamic acid tetrapeptide [SEQ ID NO: 32] and the tetrameric zipper variant corresponding to amino acids 250–281 [SEQ ID NO: 6] of GCN4.

B8. Plasmid pGEMhump53LZ346E352I

This plasmid is a modification of plasmid pGEMhump53LZ346E. A Cla I restriction site was introduced just after the last codon of pGEMhump53LZ346E by PCR with the primer GTCATCGATG CGTTCGCCAA CTAATTTCTT [SEQ ID NO: 33]. A PCR fragment encoding residues 352–393 of human p53 [SEQ ID NO:2] containing a Cla I site at its 5' end was also generated using the primer ATGAGGCCTT GGAACTCATC GATGCCCAGG CTGGG of SEQ ID NO: 34. The latter fragment was cloned using the Cla I-Sal I sites into the modified (using the primer of SEQ ID NO: 33) pGEMhump53LZ346E vector. The resultant plasmid, pGEMhump53LZ346E352I, encodes amino acids 1–346 of human p53 [SEQ ID NO: 2], a glutamic acid, the leucine zipper corresponding to amino acids 253–281 of GCN4 [SEQ ID NO: 4], an isoleucine and then residues 352–393 of human p53 [SEQ ID NO: 2].

B9. Plasmid pGEMhump53TZ334N352I

This plasmid is a modification of plasmid pGEMhump53TZ334N. A Cla I restriction site was introduced just after the last codon of pGEMhump53TZ334N by PCR with the primer TTTGTCGACT CAATCGATAC GTTCACCCAA TAATTTTTTG [SEQ ID NO: 35]. A PCR fragment encoding residues 352–393 of human p53 [SEQ ID NO:2] containing a Cla I site at its 5' end was also generated using the primer ATGAGGCCTT GGAACTCATC GATGCCCAGG CTGGG of SEQ ID NO: 34. The latter fragment was cloned using the Cla I-Sal I sites into the modified (using the primer of SEQ ID NO: 35) pGEMhump53TZ334N vector. The resultant plasmid, pGEMhump53TZ334N352I, encodes amino acids 1–334 of human p53 [SEQ ID NO: 2], an asparagine, the tetrameric zipper variant corresponding to amino acids 249–281 [SEQ ID NO: 6] of GCN4, an isoleucine and then residues 352–393 of human p53 [SEQ ID NO: 2].

B10. Plasmids pGEMhump53H175, pGEMhump53Q334, pGEMhump53L337, pGEMhump53A341 and pGEMhump53A344

Plasmids pGEMhump53H175, pGEMhump53Q334, pGEMhump53L337, pGEMhump53A341 and pGEMhump53A344 encode proteins that differ by one amino acid from wild-type human p53 [SEQ ID NO: 2]. Specifically, they substitute Arg175 with His, Gly334 with Gln, Arg337 with Leu, Phe341 with Ala and Leu344 with Ala of p53 SEQ ID NO: 2, respectively. These single amino acid substitutions were generated using standard recombinant techniques [Ausubel et al, (1994), cited above; Innis et al, (1990), cited above]. Substitution of Arg175 of SEQ ID NO: 2 with His is often associated with human tumors.

B11. Plasmids pGEMhump53D290-297, pGEMhump53D290-297D300-321, pGEMhump53D300-308, pGEMhump53D300-317, pGEMhump53D300-321, pGEMhump53D300-327, and pGEMhump53D364-393

Plasmids pGEMhump53D290-297, pGEMhump53D290-297D300-321, pGEMhump53D300-308, pGEMhump53D300-317, pGEMhump53D300-321, pGEMhump53D300-327, and pGEMhump53D364-393 encode proteins that contain deletions within wild-type human p53 [SEQ ID NO: 2]. These deletions involve residues 290–297, 290–297 and 300–321, 300–308, 300–317, 300–321, 300–327 and 364–393 of p53 SEQ ID NO: 2, respectively. These deletions were generated using standard recombinant techniques [Ausubel et al, (1994), cited above; Innis et al, (1990), cited above].

C. Plasmid pSV2hump53wt

Plasmid pSV2hump53wt encodes full-length human wild-type p53 [SEQ ID NO: 2], and directs transcription of this protein in mammalian cells. The pSV2 vector has been previously described [Mulligan et al, (1981), Proc. Natl. Acad. Sci. USA, 78:2072–2076]. A pSV2 vector containing a human c-jun insert has also been described [Zhang et al, (1990), Proc. Natl. Acad. Sci. USA, 87:6281–6285]. The c-jun insert was removed from the latter plasmid using Sal I and Bgl II restriction endonucleases, and the ends of the vector were blunted. Into this vector a blunted Eco RI-Hind III p53 insert from pGEMhump53wt was cloned.

D. Plasmids of the pSV2hump53 Series Encoding p53 Proteins with Altered Tetramerization Domains Because plasmids pGEMhump53wt and pSV2hump53wt contain the same p53 insert, it is possible to use restriction sites that are common within the inserts of these plasmids, to transfer p53 subfragments from plasmids of the pGEMhump53 series to pSV2hump53wt. Specifically, it is possible to transfer, for example, Sst II-Sal I fragments encoding altered tetramerization domains into the pSV2hump53 vector, and thus allow expression of p53 proteins of the invention in mammalian cells.

pSV2 vectors expressing most of the proteins described above have been constructed. The name of the p53 protein with altered tetramerization domain is retained from the pGEM to the pSV2 series. For example, transfer of the Sst II-Sal I fragment of pGEMhump53TZ334N to pSV2hump53wt, yields pSV2hump53TZ334N, which allows expression in mammalian cells of a p53 protein containing amino acids 1–334 of human p53 [SEQ ID NO: 2], an asparagine, and then the tetrameric zipper variant corresponding to amino acids 249–281 [SEQ ID NO: 6] of GCN4.

E. Reporter Plasmids To Assay p53-Mediated Transcriptional Activity

The reporter plasmids drive expression of alkaline phosphatase in a p53-dependent manner. Plasmids pEwaf1-TK-SEAP, pBC.V4A-TK-SEAP and pBC-TK-SEAP have one copy each of double-stranded oligonucleotides Ewaf1 [SEQ ID NO: 16], BC.V4A [SEQ ID NO: 17] and BC [SEQ ID NO: 18], respectively cloned into the unique Eco RV site of pTK-SEAP. These oligonucleotides contain p53 binding sites of different affinities.

The sequence of oligonucleotide Ewaf1 (top strand) is: CCC-GAACA-TGTCC-CAACA-TGTTG-GGG [SEQ ID NO: 16]. This oligonucleotide corresponds to the enhancer that drives p53-dependent transcription of the waf1 gene [El-DeiryDeiry et al, (1993), cited above]. The sequence of oligonucleotide BC.V4A (top strand) is: TC-GAGCA-TGTTC-GAGCA-TGTTC-GAGCATGT [SEQ ID NO: 17], and the sequence of oligonucleotide BC (top strand) is: CC-GGGCA-TGTCC-GGGCA-TGTCC-GGGCATGT [SEQ ID NO: 18]. Oligonucleotides BC.V4A [SEQ ID NO: 17] and BC [SEQ ID NO: 18] contain artificial sites recognized by p53. For the three sites indicated above, the specific pentanucleotide repeats recognized by p53 are demarcated by hyphens.

Plasmid pTK-SEAP drives expression of a secreted form of alkaline phosphatase under the control of a minimal thymidine kinase promoter [Halazonetis (1992), Anticancer Res., 12:285–292]. It contains no p53 binding site, and thus serves as a control.

F. Plasmid pSV2gpt

Plasmid pSV2gpt [Mulligan et al, (1981), cited above] drives expression of gpt in mammalian cells. In these studies it only serves to bring the total amount of transfected DNA to 30 µg, when necessary. Expression of gpt does not interfere with p53 function.

Example 2—In Vitro Translation and DNA Binding Assay

Plasmids of the pGEMhump53 series of Example 1 were used to produce in vitro transcribed mRNA according to standard procedures [Halazonetis et al, (1988), cited above]. The mRNA is subsequently translated in vitro using preferably rabbit reticulocyte lysate (Promega, Madison, Wis.) [Halazonetis et al (1988), cited above]. In vitro translated p53 can be used directly for DNA binding, without further purification.

Alternate strategies for expression of p53 for DNA binding assays include expression in E. coli or in Sf9 insect cells using appropriate vectors (many are commercially available) for expression in bacterial cells or baculovirus vectors, respectively. Lysates or extracts prepared from bacterial or insect cells are used without purification, or optimally, following partial or complete purification using standard protein purification techniques [Scopes (1994), cited above].

The in vitro translated proteins were assayed for DNA binding, as previously described [Halazonetis et al, (1993), cited above].

Briefly, as exemplified below, the in vitro translated protein is incubated with a radioactively labeled oligonucleotide containing a p53 binding site in the presence of non-specific competitor DNA. The reaction mixture is incubated 20 min. at room temperature and directly loaded on a native 5% polyacrylamide electrophoresis gel. In this type of DNA binding assay free DNA migrates to the bottom of the gel, whereas p53/DNA complexes migrate more slowly. Thus, the presence of slowly migrating DNA, which can be detected by autoradiography, indicates p53 DNA binding [Halazonetis et al (1993), cited above; Halazonetis and Kandil (1993), cited above].

As non-specific competitor DNAs, the following were used: 0.1 µg single-stranded oligonucleotide MI7 [GAGAGCCCCAGTTACCATAACTACTCT, SEQ ID NO: 36] and 0.05 µg double-stranded oligonucleotide TF3 [ATCACGTGATATCACGTGATATCACGTGAT, SEQ ID NO: 37] per reaction.

A number of double-stranded oligonucleotides containing p53 binding sites were radioactively labeled for these experiments. These included oligonucleotides Ewaf1, BC.V4A and BC [SEQ ID NOS: 16, 17 and 18, respectively], and oligonucleotide BC.S21. The sequence of BC.S21 is: TAT-GGGCA-TGTCC-TATATATATGCG-TATATAT-GGGCA-TGTCC-TAT [SEQ ID NO: 19]. The pentanucleotide repeats, which are recognized by p53, are indicated by hyphens. These DNAs were radioactively labeled using 32P-labeled nucleotides, as described [Halazonetis et al, (1988), cited above].

Results using this assay are presented in Example 3, below.

Example 3—DNA Binding Activities of p53 Proteins with Altered Tetramerization Domains A. DNA Binding Activities of Wild-type Human p53

The ability of wild-type human p53 to recognize the DNA sites present in oligonucleotides Ewaf1, BC.V4A and BC [SEQ ID NOS: 16, 17 and 18, respectively] has been previously demonstrated [El-DeiryDeiry et al, (1993), cited above; Halazonetis et al, (1993), cited above]. Using the assay described in Example 2, wild-type p53 recognized all these DNAs. The highest signal was obtained using the BC oligonucleotide [SEQ ID NO: 18], while oligonucleotide Ewaf1 [SEQ ID NO: 16] gave the weakest signal. The intensity of the signal in this assay reflects the affinity of p53 for the different DNA sites. The intensity of the signal using oligonucleotides BC.V4A [SEQ ID NO: 17] or Ewaf1 [SEQ ID NO: 16] was enhanced in the presence of 0.1 µg anti-p53 antibody PAb421 [Oncogene Science, Uniondale, N.Y.]. This antibody activates DNA binding of wild-type p53, by switching the conformation of the protein [Halazonetis et al, (1993), cited above; Halazonetis and Kandil (1993), cited above]. Binding to oligonucleotide BC [SEQ ID NO: 18] is quite potent, and very little further enhancement is observed following incubation with antibody PAb421. In addition to antibody PAb421, the conformation of p53 can be switched by a C-terminal truncation that removes residues 364–393 of human p53 [SEQ ID NO: 2] [Halazonetis and Kandil (1993), cited above; Hupp et al (1992), Cell, 71:875–886; Hupp and Lane (1994), Current Biology, 4:865–875]. The C-terminally truncated p53 protein, p53D364-393, bound all three oligonucleotides with high affinity, comparable to wild-type p53 in the presence of PAb421.

Binding of wild-type p53 to oligonucleotide BC.S21 was also examined. This oligonucleotide [SEQ ID NO: 19] contains two pairs of contiguous pentanucleotide repeats separated by 21 nucleotides. Wild-type p53 bound efficiently to this DNA, as indicated by a strong signal in the DNA binding assay described in Example 2, above. The signal was as strong as with oligonucleotide BC [SEQ ID NO: 18] (which represents the optimal p53 DNA site) and was not further enhanced by antibody PAb421. As discussed in the Section V.B1, oligonucleotide BC.S21 [SEQ ID NO: 19] does not match the consensus p53 DNA site. Thus, the ability of wild-type p53 to bind to oligonucleotide BC.S21 [SEQ ID NO: 19] is a novel finding.

B. DNA Binding Activities of p53LZ346E, p53LZ347, p53TZ334N and p53TZ323RGN

Proteins p53LZ346E, p53LZ347, p53TZ334N and p53TZ323RGN represent chimeric proteins of the invention, which are encoded by plasmids pGEMhump53LZ346E, pGEMhump53LZ347, pGEMhump53TZ334N and pGEMhump53TZ323RGN, respectively, described in Example 1. The ability of these proteins to bind oligonucleotides Ewaf1, BC.V4A and BC [SEQ ID NOS: 16, 17 and 18, respectively] was examined using the assay described in Example 2. All of them bound to all three oligonucleotides. The signal intensities were overall comparable to those of wild-type p53 bound to the respective oligonucleotides in the presence of PAb421 or to those of p53D364-393 bound to the respective oligonucleotides. p53LZ347, p53TZ334N and p53TZ323RGN exhibited somewhat higher affinity for DNA, as compared to p53LZ346E.

The DNA complexes of proteins p53LZ346E, p53LZ347, p53TZ334N and p53TZ323RGN comigrated with the DNA complex of wild-type p53 or the DNA complex of p53D364-393. Since migration on acrylamide gels depends on the molecular size of the migrating species [Hope and Struhl (1987), EMBO J., 6:2781–2784] this indicates that the complexes of wild-type p53, p53D364-393, p53LZ346E, p53LZ347, p53TZ334N and p53TZ323RGN with DNA have similar molecular sizes. Since wild-type p53 and p53D364-393 bind DNA as tetramers [Halazonetis and Kandil (1993), cited above; Cho et al, (1994), cited above;

Hupp and Lane (1994), cited above], then p53LZ346E, p53LZ347, p53TZ334N and p53TZ323RGN also bind DNA as tetramers.

C. DNA Binding Activities of p53LZ335Q and p53LZ343

Proteins p53LZ335Q and p53LZ343 are chimeric proteins of p53 with the GCN4 leucine zipper, encoded by plasmids pGEMhump53LZ335Q and pGEMhump53LZ343, respectively. Protein p53LZ343 was first described by Pietenpol et al, (1994) [cited above]. The ability of these proteins to bind oligonucleotides BC.V4A and BC [SEQ ID NOS: 17 and 18, respectively] was examined using the assay described in Example 2. Both bound to oligonucleotide BC [SEQ ID NO: 18] (the optimal p53 DNA site [Halazonetis et al, (1993), cited above], but neither bound oligonucleotide BC.V4A [SEQ ID NO: 17] (a suboptimal site). Thus, the DNA binding activities of these proteins are compromised relative to wild-type p53. In addition the complexes of p53LZ335Q and p53LZ343 with oligonucleotide BC [SEQ ID NO: 18] migrate significantly faster than the corresponding complexes of wild-type p53 or p53D364-393. Thus, the molecular sizes of the complexes of p53LZ335Q and p53LZ343 are smaller than those of wild-type p53 or p53D364-393. Since wild-type p53 and p53D364-393 are tetramers [Halazonetis and Kandil (1993), cited above; Cho et al, (1994), cited above; Hupp and Lane (1994), cited above], p53LZ335Q and p53LZ343 are dimers. They cannot be monomers, because monomeric p53 does not bind DNA [Halazonetis and Kandil (1993), cited above].

In conclusion the ability of p53 proteins with altered tetramerization domains to bind to the full panel of p53 DNA sites correlates with their ability to form tetramers. Furthermore, p53LZ335Q and p53LZ343 are not proteins of this invention, since they fail to form tetramers.

D. DNA Binding Activities of p53Q334, p53L337, p53A341 and p53A344

Proteins p53Q334, p53L337, p53A341 and p53A344 are encoded by plasmids pGEMhump53Q334, pGEMhump53L337, pGEMhump53A341 and pGEMhump53A344, respectively, described in Example 1. The ability of these proteins to bind oligonucleotide BC [SEQ ID NO: 18] was examined using the assay described in Example 2. Proteins p53Q334, p53L337 and p53A341 bound DNA very weakly, if at all. This finding indicates that these substitutions disrupt completely the function of the p53 tetramerization domain, because they map within the tetramerization domain [Wang et al, (1994), cited above; Clore et al, (1994), cited above] and DNA binding by p53 requires oligomerization [Halazonetis and Kandil (1993), cited above].

Protein p53A344 bound oligonucleotide BC [SEQ ID NO: 18]. However, its complex with DNA migrated significantly faster than the DNA complexes of wild-type p53 or p53D364-393. Thus, p53A344 is a dimer, rather than a tetramer. Thus, this single amino acid substitution partially disrupts the function of the p53 tetramerization domain.

E. DNA Binding Activities of p53D290-297, p53D290-297D300-321, p53D300-308, p53D300-317, p53D300-321, and p53D300-327

Proteins p53D290-297, p53D290-297D300-321, p53D300-308, p53D300-317, p53D300-321 and p53D300-327 are encoded by plasmids pGEMhump53D290-297, pGEMhump53D290-297D300-321, pGEMhump53D300-308, pGEMhump53D300-317, pGEMhump53D300-321 and pGEMhump53D300-327, respectively, described in Example 1. The ability of these proteins to bind oligonucleotides BC and BC.S21 [SEQ ID NOS: 18 and 19, respectively] was examined using the assay described in Example 2. Proteins p53D290-297, p53D300-308, p53D300-317, and p53D300-321 bound both oligonucleotides BC and BC.S21 [SEQ ID NOS: 18 and 19, respectively] with efficiencies paralleling that of wild-type p53. In addition the complexes of these proteins with DNA comigrated with the complexes of wild-type p53 with DNA. Thus, p53D290-297, p53D300-308, p53D300-317 and p53D300-321 exhibit DNA binding properties similar to wild-type p53.

Proteins p53D290-297D300-321 and p53D300-327 formed aberrant complexes with oligonucleotide BC [SEQ ID NO: 18]. These complexes migrated very slowly and the signal intensity was very low. In contrast, the complexes of p53D290-297D300-321 and p53D300-327 with oligonucleotide BC.S21 [SEQ ID NO: 19], were similar to those of wild-type p53. Proteins p53D290-297D300-321 and p53D300-327 have diminished ability to recognize oligonucleotide BC [SEQ ID NO: 18], but their ability to recognize oligonucleotide BC.S21 [SEQ ID NO: 19] is intact.

Example 4—Immunoprecipitation of p53 Proteins

For immunoprecipitation experiments the p53 proteins were in vitro translated, as described in Example 2, in the presence of 35S-methionine, so that they would be radioactively labeled. Following in vitro translation, 3 μl of the lysate containing the translated protein(s) was incubated in 30 μl DNA binding buffer [Halazonetis et al, (1993), cited above] for 20 minutes at room temperature. Then 0.6 μg anti-p53 antibody PAb421 [Oncogene Science, Uniondale, N.Y.], 30 μl packed protein G-Sepharose beads [Pharmacia, Piscataway, N.J.] and 400 μl high-salt/EDTA immunoprecipitation buffer [Halazonetis et al, (1993), cited above] were added. After 45 min incubation at room temperature on a rotator, the beads were washed three times with the high-salt/EDTA immunoprecipitation buffer and the proteins absorbed to the beads were eluted with SDS sample buffer and subjected to SDS-PAGE.

The use of this assay is described in Example 5 below.

Example 5—Hetero-Oligomerization Assay

This assay was used to demonstrate that p53LZ346E, one of the proteins of the invention encoded by plasmid pGEMhump53LZ346E (Example 1), does not hetero-oligomerize with p53 proteins having intact native p53 tetramerization domains, such as wild-type p53 and tumor-derived p53 mutants.

Wild-type p53 and p53LZ346E were cotranslated in the presence of 35S-methionine. Simultaneous translation of the two proteins provides opportunity for the two different subunit types to form hetero-oligomers. After cotranslation was completed, the mixture was immunoprecipitated using antibody PAb421, as described in Example 4 above.

The epitope of antibody PAb421 maps to residues 373–381 of human p53 [SEQ ID NO: 2]. Therefore, PAb421 recognizes wild-type p53, but not p53LZ346E. Thus, if the two proteins hetero-oligomerize when cotranslated, then both will be precipitated by PAb421. If they do not hetero-oligomerize, then only wild-type p53 will be precipitated.

Following SDS-polyacrylamide gel electrophoresis, a radioactive band migrating like wild-type p53 was noted. No band corresponding to p53LZ346E was observed. These results indicate that wild-type p53 and p53LZ346E do not hetero-oligomerize. As a positive control the ability of wild-type p53 and p53D364-393 to hetero-oligomerize using this assay was examined. Like p53LZ346E, p53D364-393 lacks the epitope for PAb421. However, p53D364-393 has an intact native p53 tetramerization domain. When cotranslated with wild-type p53, both wild-type p53 and p53D364-393 were precipitated by PAb421, indicating that wild-type p53 and p53D364-393 form hetero-oligomers.

Example 6—Transcriptional Activity Assay

An assay for transcriptional activity entails introducing vectors expressing wild-type p53 or p53 proteins of the invention into cells together with a reporter plasmid that expresses a reporter marker in a p53-dependent manner. Preferably the cells are human tumor cells that do not express endogenous p53, so that the transcriptional activity can be evaluated without interference from endogenous wild-type or mutant p53. [See, e.g., Lin et al, (1994), cited above; Wu et al, (1993), cited above; Chen et al, (1993), Oncogene, 8:2159–2166; Chumakov et al, (1993), Oncogene, 8:3005–3011; Unger et al, (1992), EMBO J, 11:1383–1390; Kern et al, (1992), Science, 256:827–830; Pietenpol et al, (1994), cited above].

Transcriptional activity was assayed in Saos-2 human osteosarcoma cells [ATCC HTB 85]. These cells do not contain any endogenous p53, because both p53 alleles are deleted [Diller et al, (1990), Mol. Cell. Biol., 10:5772–5781]. Thus, any transcriptional activity can be attributed to the transfected p53. Transcriptional activity was assayed as previously described [Halazonetis (1992), Anticancer Res., 12:285–292]. Briefly, plasmids expressing p53 in mammalian cells (of the pSV2 series described in Example 1) were cotransfected with reporter plasmids (of the pTK-SEAP series described in Example 1) using the calcium phosphate technique [Halazonetis (1992), cited above]. Alkaline phosphatase activity, which reflects p53-mediated transcriptional activity, was assayed as previously described [Halazonetis (1992), cited above].

The use of this assay is described in Examples 7 and 8 below.

Example 7—Comparison of Transcriptional Activities of Wild-type p53, p53LZ346E, p53LZ347, p53LZ335Q, p53LZ343 and p53TZ334N Wild-type p53, p53LZ346E, p53LZ347, p53LZ335Q, p53LZ343 and p53TZ334N were expressed in Saos-2 cells [ATCC HTB 85] by transfecting plasmids pSV2hump53wt, pSV2hump53LZ346E, pSV2hump53LZ347, pSV2hump53LZ335Q, pSV2hump53LZ343 and pSV2hump53TZ334N, respectively. The transcriptional activities of the expressed proteins were assayed using one or more of the reporter plasmids pBC-TK-SEAP, pBC.V4A-TK-SEAP and pEwaf1-TK-SEAP, described in Example 1.

Results of representative experiments are presented in Table 1 below. The units of transcriptional activity are relative, and comparisons should only be made within the same experiment. For each transfection the amounts of transfected plasmid are indicated in µg. Where the total amount was less than 30 µg, then plasmid pSV2gpt (described in Example 1) was used to bring the total to 30 µg.

TABLE 1

| Experiment 1 Reporter Plasmid: 10 µg pBC.V4A-TK-SEAP | |
|---|---|
| p53 Expression Plasmid (2 µg) | Transcriptional Activity |
| pSV2hump53wt | 1700 |
| pSV2hump53LZ347 | 524 |
| pSV2hump53LZ335Q | 18 |
| pSV2hump53LZ343 | 22 |

TABLE 1-continued

| Experiment 2 Reporter Plasmid: 10 µg pEwaf1-TK-SEAP | | |
|---|---|---|
| p53 Expression Plasmid (3 µg) | | Transcriptional Activity |
| pSV2hump53wt | | 1990 |
| pSV2hump53LZ346E | | 520 |
| Experiment 3 p53 Expression Plasmid (15 µg) | Reporter Plasmid (15 µg) | Transcriptional Activity |
| pSV2hump53wt | pEwaf1-TK-SEAP | 1640 |
| pSV2hump53TZ334N | pEwaf1-TK-SEAP | 1480 |
| pSV2hump53TZ334N | pBC.V4A-TK-SEAP | 2750 |
| pSV2hump53TZ334N | PBC-TK-SEAP | 2550 |

From the results of Table 1 it is apparent that wild-type p53 is able to activate transcription from all the reporter plasmids examined, including plasmid pEwaf1-TK-SEAP, which contains the weakest p53 binding site. The tetrameric p53 proteins of the invention: p53LZ346E, p53LZ347 and p53TZ334N, all exhibit transcriptional activity. In contrast the dimeric p53 chimeric proteins, such as p53LZ335Q and p53LZ343, do not exhibit transcriptional activity that is detectably above background in this assay, and are thus clearly inferior to the tetrameric proteins of this invention. It is possible that the dimeric proteins may exhibit higher transcriptional activity when grossly overexpressed, since Pietenpol et al, (1994) [cited above] have reported detectable transcriptional activity using protein p53LZ343. The inventor has been unable to reproduce this result, as the Experiments of Table 1 indicate. Even if p53LZ343 has detectable transcriptional activity when grossly overexpressed, our experiments indicate that the tetrameric p53 proteins of this invention are clearly superior to the dimeric proteins.

Example 8—Ability of Tumor-Derived p53 Mutants to Suppress the Transcriptional Activities of wild-Type p53 or Tetrameric D53 Proteins of the Invention Tumor-derived p53 mutants are known to suppress the transcriptional activity of wild-type p53 by forming hetero-tetramers with wild-type p53 [Milner and Medcalf (1991), cited above; Bargonetti et al, (1992), cited above; Farmer et al, (1992), cited above; Kern et al, (1992), cited above]. The tetrameric p53 proteins of this invention do not hetero-tetramerize with tumor-derived p53 mutants, because the native p53 tetramerization domain is partially or completely disrupted (See Example 5). Consequently, the transcriptional activities of the tetrameric p53 proteins should not be inhibited by tumor-derived p53 mutants.

To establish this, the transcriptional activities of the p53 proteins of this invention in the presence of excess of a tumor-derived p53 mutant were compared to their transcriptional activities in the absence of the tumor-derived mutant. The tumor-derived p53 mutant is expressed in cells using a suitable vector (as described in Example 1). Preferably, the tumor-derived mutant should be in 5 to 20-fold or more excess relative to the p53 protein of the invention, which can be roughly achieved by transfecting into the cells 5 to 20-fold or more excess vector expressing the tumor-derived p53 mutant over the vector expressing the protein of the invention.

Tumor-derived mutants, p53His175 and p53Ser249 are suitable for these studies because they potently inhibit the transcriptional activity of wild-type p53. These mutants have histidine at position 175 or serine at position 249 of human p53 [SEQ ID NO: 2], respectively. Other tumor-derived p53 mutants [Caron de Fromentel and Soussi (1992), Genes Chrom. Cancer, 4:114 15] can also be used, as long as they potently inhibit the transcriptional activity of wild-type p53.

Results of relevant Experiments are presented in Table 2 below. Suppression of transcriptional activity by the tumor-derived p53 mutant is presented as percent of residual transcriptional activity in the presence of the tumor-derived p53 mutant, as compared to the transcriptional activity in the absence of the mutant. For each transfection the amounts of transfected plasmids are indicated in μg. Where the total amount was less than 30 μg (as in the absence of the tumor-derived p53 mutant), then plasmid pSV2gpt (described in Example 1) was used to bring the total to 30 μg. For these experiments the tumor-derived p53 mutant His 175 was used (described in Example 1).

TABLE 2

Experiment 1
Reporter Plasmid: 10 μg pBC-TK-SEAP
Plasmid for Tumor-Derived p53 Mutant: 19 μg pSV2hump53H175

| p53 Expression Plasmid (1 μg) | Residual Transcriptional Activity in the Presence of Tumor-Derived p53 Mutant |
|---|---|
| pSV2hump53wt | 23% |
| pSV2hump53LZ346E | 100% |

TABLE 2-continued

| pSV2hump53LZ347 | 46% |

Experiment 2
Reporter Plasmid: 10 μg pBC.V4A-TK-SEAP
Plasmid for Tumor-Derived p53 Mutant: 19 μg pSV2hump53H175

| p53 Expression Plasmid (1 μg) | Residual Transcriptional Activity in the Presence of Tumor-Derived p53 Mutant |
|---|---|
| pSV2hump53wt | 2% |
| pSV2hump53TZ334N | 80% |

From the results of the experiments presented in Table 2 it is apparent that, in contrast to wild-type p53, the transcriptional activities of the p53 tetrameric proteins of the invention are not suppressed, or only minimally suppressed, by gross excess of a tumor-derived p53 mutant.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A nucleotide sequence encoding a modified p53 protein, said modified p53 protein comprising:
   a p53 sequence consisting of amino acid residues 1 to between about 290 to about 334 of human p53 and a heterologous tetramerization domain consisting of a modified leucine zipper sequence containing isoleucines and positions d of the coiled coil and leucines at positions a,
   said modifications providing said protein with the inability to hetero-oligomerize with wild-type p53 or tumor-derived mutant p53 proteins, and said modifications not interfering with the native tumor-suppression function of the protein or with its ability to form tetramers.

2. The nucleotide sequence according to claim 1, said sequence under the control of regulatory sequences directing its replication and in vivo or in vitro expression of said protein in a selected host cell.

3. A nucleotide sequence encoding a chimeric p53 protein comprising:
   an N-terminal p53 sequence encoding amino acid residue 1 to at least residue 290 and at most residue 334;
   a heterologous tetramerization sequence consisting of a modified leucine zipper sequence containing isoleucines at positions d of the coiled coil and leucines at positions a; and
   a C-terminal p53 fragment spanning amino acids about 352 to 393,
   said modifications providing said protein with the inability to hetero-oligomerize with wild-type p53 or tumor-derived mutant p53 proteins and said modifications not interfering with the native tumor-suppression function of p53 or with its ability to form tetramers.

4. The nucleotide sequence according to claim 1 or claim 3, encoding a protein having the DNA binding and transcriptional functions characteristic of wild-type p53.

5. The nucleotide sequence according to claim 1 wherein said N-terminal p53 sequence is derived from the full-length sequence by deletion of the residues selected from the group consisting of amino acids 301–393, amino acids 324–393, amino acids 326–393 and amino acids 335–393 of SEQ ID NO: 2.

6. A nucleotide sequence encoding a modified p53 protein selected from the group consisting of:
   (a) a p53 sequence spanning, from N-terminus to C-terminus, residues 1–334 of SEQ ID NO: 2, an Asn linker, and a heterologous sequence spanning residues 249–281 of SEQ ID NO: 6 containing isoleucines at positions d of the coiled coil and leucines at positions a;
   (b) a p53 sequence spanning, from N-terminus to C-terminus, residues 1–334 of SEQ ID NO: 2, a Gly-Asn-Pro-Glu SEQ ID NO: 32 linker, and a heterologous sequence spanning residues 250–281 of SEQ ID NO: 6 containing isoleucines at positions d of the coiled coil and leucines at positions a;
   (c) a p53 sequence spanning, from N-terminus to C-terminus, residues 1–325 of SEQ ID NO: 2, an Arg-Gly-Asn SEQ ID NO: 7 linker, and the heterologous sequence of (a) above;

(d) a p53 sequence spanning, from N-terminus to C-terminus, residues 1–325 of SEQ ID NO: 2, an Arg-Gly-Gly-Asn-Pro-Glu SEQ ID NO: 8 linker, and the heterologous sequence of (b) above;

(e) a p53 sequence spanning, from N-terminus to C-terminus, residues 1–323 of SEQ ID NO: 2, an Arg-Gly-Asn SEQ ID NO: 7 linker, and the heterologous sequence of (a) above;

(f) a p53 sequence spanning, from N-terminus to C-terminus, residues 1–323 of SEQ ID NO: 2, an Arg-Gly-Gly-Asn-Pro-Glu SEQ ID NO: 8 linker, and the heterologous sequence of (b) above; and (g) a p53 sequence spanning, from N-terminus to C-terminus, residues 1–300 of SEQ ID NO: 2, a Gly-Gly-Asn-Gln-Ala SEQ ID NO: 9 linker, and the heterologous sequence of (b) above.

7. A nucleotide sequence encoding a modified p53 protein having restricted DNA binding specificity which comprises a human p53 sequence and a selected heterologous tetramerization domain, wherein said p53 sequence contains a deletion selected from the group consisting of a single deletion of amino acids 300–327 of SEQ ID NO: 2 and a double deletion of amino acids 290–297 and 300–321 of SEQ ID NO: 2, wherein said deletion disrupts the native p53 tetramerization domain.

8. A nucleotide sequence encoding a modified p53 protein comprising amino acid residues 1 to about 290 of human p53 and a heterologous tetramerization domain consisting of a leucine zipper which has been modified to contain isoleucines at positions d and leucines at positions a of the leucine zipper coil, said modified p53 protein characterized by the inability to hetero-oligomerize with wild-type p53 or tumor-derived mutant p53 proteins and not interfering with the native tumor-suppression function of the p53 protein or with its ability to form tetramers.

9. A nucleotide sequence encoding a chimeric p53 protein selected from the group consisting of:

(a) a p53 sequence spanning, from N-terminus to C-terminus, residues 1–325 of SEQ ID NO: 2, an Arg-Gly-Asn SEQ ID NO: 7 linker, and a heterologous sequence spanning residues 249–281 of SEQ ID NO: 6 containing isoleucines at positions d of the coiled coil and leucines at positions a, an Ile linker, and a p53 sequence spanning residues 352–393 of SEQ ID NO: 2;

(b) a p53 sequence spanning, from N-terminus to C-terminus, residues 1–325 of SEQ ID NO: 2, an Arg-Gly-Gly-Asn-Pro-Glu SEQ ID NO: 8 linker, the heterologous sequence spanning residues 250–281 of SEQ ID NO: 6 containing isoleucines at positions d of the coiled coil and leucines at positions a, an Ile linker, and a p53 sequence spanning residues 352–393 of SEQ ID NO: 2;

(c) a p53 sequence spanning, from N-terminus to C-terminus, residues 1–323 of SEQ ID NO: 2, an Arg-Gly-Asn SEQ ID NO: 7 linker, the heterologous sequence of (a) above, an Ile linker, and a p53 sequence spanning residues 352–393 of SEQ ID NO: 2;

(d) a p53 sequence spanning, from N-terminus to C-terminus, residues 1–323 of SEQ ID NO: 2, an Arg-Gly-Gly-Asn-Pro-Glu SEQ ID NO: 8 linker, the heterologous sequence of (b) above, an Ile linker, and a p53 sequence spanning residues 352–393 of SEQ ID NO: 2; and (e) a p53 sequence spanning, from N-terminus to C-terminus, residues 1–334 of SEQ ID NO: 2, an Asn linker, the heterologous sequence of (a) above, an Ile linker, and a p53 sequence spanning residues 352–393 of SEQ ID NO: 2;

(f) a p53 sequence spanning, from N-terminus to C-terminus, residues 1–300 of SEQ ID NO:2, a Gly-Gly-Asn-Gln-Ala SEQ ID NO:9 linker, the heterologous sequence of (b) above, an Ile linker, and a p53 sequence spanning residues 352–393 of SEQ ID NO:2; and (g) a p53 sequence spanning, from N-terminus to C-terminus, residues 1–334 of SEQ ID NO:2, a Gly-Asn-Pro-Glu SEQ ID NO:32 linker, a heterologous sequence of (b) above, an Ile linker, and a p53 sequence spanning residues 352–393 of SEQ ID NO:2.

10. The nucleotide sequence according to claim 3 or 8, said sequence under the control of regulatory sequences directing its replication and in vivo or in vitro expression of said protein in a selected host cell.

11. The nucleotide sequence according to any of claims 1 or 8 encoding a protein wherein the leucine zipper sequence is derived from a protein selected from the group consisting of Jun, Max, GCN4, c-myc, c-fos, and C/EBP.

12. The nucleotide sequence according to claim 11 encoding a protein wherein the leucine zipper sequence is amino acid residues 249 to 281 of GCN4 (SEQ ID NO:6).

13. The nucleotide sequence according to any of claims 1, 3 or 8, encoding a protein further comprising an amino acid linker between said p53 sequence and said heterologous tetramerization domain.

14. The nucleotide sequence according to claim 13 encoding a protein wherein said linker is selected from the group consisting of Glu, Asn, Ile, Gly-Asn, Arg-Gly-Asn SEQ ID NO: 7, Gly-Gly-Asn-Gln-Ala SEQ ID NO: 9, Arg-Gly-Gly-Asn-Pro-Glu SEQ ID NO: 8 and Gly-Asn-Pro-Glu SEQ ID NO: 32.

15. A nucleotide sequence encoding a modified p53 protein selected from the group consisting of:

(a) a p53 sequence spanning, from N-terminus to C-terminus, residues 1–346 of human p53 SEQ ID NO:2, a Glu linker, and a heterologous tetramerization domain spanning residues 253–281 of GCN4 SEQ ID NO:4; and (b) a p53 sequence spanning, from N-terminus to C-terminus, residues 1–347 of human p53 SEQ ID NO:2 and a heterologous tetramerization domain spanning residues 253–281 of GCN4 SEQ ID NO:4.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 1317 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 136..1314

( x i ) SEQUENCE DESCRIPTION: SEQ ID NO:1:

```
GTCTAGAGCC  ACCGTCCAGG  GAGCAGGTAG  CTGCTGGGCT  CCGGGGACAC  TTTGCGTTCG      60

GGCTGGGAGC  GTGCTTTCCA  CGACGGTGAC  ACGCTTCCCT  GGATTGGCAG  CCAGACTGCC     120

TTCCGGGTCA  CTGCC ATG GAG GAG CCG CAG TCA GAT CCT AGC GTC GAG CCC         171
              Met Glu Glu Pro Gln Ser Asp Pro Ser Val Glu Pro
                1               5                   10

CCT CTG AGT CAG GAA ACA TTT TCA GAC CTA TGG AAA CTA CTT CCT GAA           219
Pro Leu Ser Gln Glu Thr Phe Ser Asp Leu Trp Lys Leu Leu Pro Glu
            15                  20                  25

AAC AAC GTT CTG TCC CCC TTG CCG TCC CAA GCA ATG GAT GAT TTG ATG           267
Asn Asn Val Leu Ser Pro Leu Pro Ser Gln Ala Met Asp Asp Leu Met
        30                  35                  40

CTG TCC CCG GAC GAT ATT GAA CAA TGG TTC ACT GAA GAC CCA GGT CCA           315
Leu Ser Pro Asp Asp Ile Glu Gln Trp Phe Thr Glu Asp Pro Gly Pro
45                  50                  55                  60

GAT GAA GCT CCC AGA ATG CCA GAG GCT GCT CCC CCC GTG GCC CCT GCA           363
Asp Glu Ala Pro Arg Met Pro Glu Ala Ala Pro Pro Val Ala Pro Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 65  |     |     |     |     | 70  |     |     |     |     | 75  |     |      |
| CCA | GCA | GCT | CCT | ACA | CCG | GCG | GCC | CCT | GCA | CCA | GCC | CCC | TCC | TGG | CCC | 411  |
| Pro | Ala | Ala | Pro | Thr | Pro | Ala | Ala | Pro | Ala | Pro | Ala | Pro | Ser | Trp | Pro |      |
|     |     |     | 80  |     |     |     |     | 85  |     |     |     |     | 90  |     |     |      |
| CTG | TCA | TCT | TCT | GTC | CCT | TCC | CAG | AAA | ACC | TAC | CAG | GGC | AGC | TAC | GGT | 459  |
| Leu | Ser | Ser | Ser | Val | Pro | Ser | Gln | Lys | Thr | Tyr | Gln | Gly | Ser | Tyr | Gly |      |
|     |     | 95  |     |     |     |     | 100 |     |     |     |     | 105 |     |     |     |      |
| TTC | CGT | CTG | GGC | TTC | TTG | CAT | TCT | GGG | ACA | GCC | AAG | TCT | GTA | ACT | TGC | 507  |
| Phe | Arg | Leu | Gly | Phe | Leu | His | Ser | Gly | Thr | Ala | Lys | Ser | Val | Thr | Cys |      |
|     | 110 |     |     |     |     | 115 |     |     |     |     | 120 |     |     |     |     |      |
| ACG | TAC | TCC | CCT | GCC | CTC | AAC | AAG | ATG | TTT | TGC | CAA | CTG | GCC | AAG | ACC | 555  |
| Thr | Tyr | Ser | Pro | Ala | Leu | Asn | Lys | Met | Phe | Cys | Gln | Leu | Ala | Lys | Thr |      |
| 125 |     |     |     |     | 130 |     |     |     |     | 135 |     |     |     |     | 140 |      |
| TGC | CCT | GTG | CAG | CTG | TGG | GTT | GAT | TCC | ACA | CCC | CCG | CCC | GGC | ACC | CGC | 603  |
| Cys | Pro | Val | Gln | Leu | Trp | Val | Asp | Ser | Thr | Pro | Pro | Pro | Gly | Thr | Arg |      |
|     |     |     |     | 145 |     |     |     |     | 150 |     |     |     |     | 155 |     |      |
| GTC | CGC | GCC | ATG | GCC | ATC | TAC | AAG | CAG | TCA | CAG | CAC | ATG | ACG | GAG | GTT | 651  |
| Val | Arg | Ala | Met | Ala | Ile | Tyr | Lys | Gln | Ser | Gln | His | Met | Thr | Glu | Val |      |
|     |     |     | 160 |     |     |     |     | 165 |     |     |     |     | 170 |     |     |      |
| GTG | AGG | CGC | TGC | CCC | CAC | CAT | GAG | CGC | TGC | TCA | GAT | AGC | GAT | GGT | CTG | 699  |
| Val | Arg | Arg | Cys | Pro | His | His | Glu | Arg | Cys | Ser | Asp | Ser | Asp | Gly | Leu |      |
|     |     | 175 |     |     |     |     | 180 |     |     |     |     | 185 |     |     |     |      |
| GCC | CCT | CCT | CAG | CAT | CTT | ATC | CGA | GTG | GAA | GGA | AAT | TTG | CGT | GTG | GAG | 747  |
| Ala | Pro | Pro | Gln | His | Leu | Ile | Arg | Val | Glu | Gly | Asn | Leu | Arg | Val | Glu |      |
|     | 190 |     |     |     |     | 195 |     |     |     |     | 200 |     |     |     |     |      |
| TAT | TTG | GAT | GAC | AGA | AAC | ACT | TTT | CGA | CAT | AGT | GTG | GTG | GTG | CCC | TAT | 795  |
| Tyr | Leu | Asp | Asp | Arg | Asn | Thr | Phe | Arg | His | Ser | Val | Val | Val | Pro | Tyr |      |
| 205 |     |     |     |     | 210 |     |     |     |     | 215 |     |     |     |     | 220 |      |
| GAG | CCG | CCT | GAG | GTT | GGC | TCT | GAC | TGT | ACC | ACC | ATC | CAC | TAC | AAC | TAC | 843  |
| Glu | Pro | Pro | Glu | Val | Gly | Ser | Asp | Cys | Thr | Thr | Ile | His | Tyr | Asn | Tyr |      |
|     |     |     |     | 225 |     |     |     |     | 230 |     |     |     |     | 235 |     |      |
| ATG | TGT | AAC | AGT | TCC | TGC | ATG | GGC | GGC | ATG | AAC | CGG | AGA | CCC | ATC | CTC | 891  |
| Met | Cys | Asn | Ser | Ser | Cys | Met | Gly | Gly | Met | Asn | Arg | Arg | Pro | Ile | Leu |      |
|     |     |     | 240 |     |     |     |     | 245 |     |     |     |     | 250 |     |     |      |
| ACC | ATC | ATC | ACA | CTG | GAA | GAC | TCC | AGT | GGT | AAT | CTA | CTG | GGA | CGG | AAC | 939  |
| Thr | Ile | Ile | Thr | Leu | Glu | Asp | Ser | Ser | Gly | Asn | Leu | Leu | Gly | Arg | Asn |      |
|     |     | 255 |     |     |     |     | 260 |     |     |     |     | 265 |     |     |     |      |
| AGC | TTT | GAG | GTG | CGT | GTT | TGT | GCC | TGT | CCT | GGG | AGA | GAC | CGG | CGC | ACA | 987  |
| Ser | Phe | Glu | Val | Arg | Val | Cys | Ala | Cys | Pro | Gly | Arg | Asp | Arg | Arg | Thr |      |
|     | 270 |     |     |     |     | 275 |     |     |     |     | 280 |     |     |     |     |      |
| GAG | GAA | GAG | AAT | CTC | CGC | AAG | AAA | GGG | GAG | CCT | CAC | CAC | GAG | CTG | CCC | 1035 |
| Glu | Glu | Glu | Asn | Leu | Arg | Lys | Lys | Gly | Glu | Pro | His | His | Glu | Leu | Pro |      |
| 285 |     |     |     |     | 290 |     |     |     |     | 295 |     |     |     |     | 300 |      |
| CCA | GGG | AGC | ACT | AAG | CGA | GCA | CTG | CCC | AAC | AAC | ACC | AGC | TCC | TCT | CCC | 1083 |
| Pro | Gly | Ser | Thr | Lys | Arg | Ala | Leu | Pro | Asn | Asn | Thr | Ser | Ser | Ser | Pro |      |
|     |     |     |     | 305 |     |     |     |     | 310 |     |     |     |     | 315 |     |      |
| CAG | CCA | AAG | AAG | AAA | CCA | CTG | GAT | GGA | GAA | TAT | TTC | ACC | CTT | CAG | ATC | 1131 |
| Gln | Pro | Lys | Lys | Lys | Pro | Leu | Asp | Gly | Glu | Tyr | Phe | Thr | Leu | Gln | Ile |      |
|     |     |     | 320 |     |     |     |     | 325 |     |     |     |     | 330 |     |     |      |
| CGT | GGG | CGT | GAG | CGC | TTC | GAG | ATG | TTC | CGA | GAG | CTG | AAT | GAG | GCC | TTG | 1179 |
| Arg | Gly | Arg | Glu | Arg | Phe | Glu | Met | Phe | Arg | Glu | Leu | Asn | Glu | Ala | Leu |      |
|     |     | 335 |     |     |     |     | 340 |     |     |     |     | 345 |     |     |     |      |
| GAA | CTC | AAG | GAT | GCC | CAG | GCT | GGG | AAG | GAG | CCA | GGG | GGG | AGC | AGG | GCT | 1227 |
| Glu | Leu | Lys | Asp | Ala | Gln | Ala | Gly | Lys | Glu | Pro | Gly | Gly | Ser | Arg | Ala |      |
|     | 350 |     |     |     |     | 355 |     |     |     |     | 360 |     |     |     |     |      |
| CAC | TCC | AGC | CAC | CTG | AAG | TCC | AAA | AAG | GGT | CAG | TCT | ACC | TCC | CGC | CAT | 1275 |
| His | Ser | Ser | His | Leu | Lys | Ser | Lys | Lys | Gly | Gln | Ser | Thr | Ser | Arg | His |      |
| 365 |     |     |     |     | 370 |     |     |     |     | 375 |     |     |     |     | 380 |      |
| AAA | AAA | CTC | ATG | TTC | AAG | ACA | GAA | GGG | CCT | GAC | TCA | GAC | TGA |     |     | 1317 |
| Lys | Lys | Leu | Met | Phe | Lys | Thr | Glu | Gly | Pro | Asp | Ser | Asp |     |     |     |      |

385                          390

(2) INFORMATION FOR SEQ ID NO:2:

(i) SEQUENCE CHARACTERISTICS:
       (A) LENGTH: 393 amino acids
       (B) TYPE: amino acid
       (D) TOPOLOGY: linear (ii) MOLECULE TYPE: protein (xi) SEQUENCE DESCRIPTION: SEQ ID NO:2:

| Met | Glu | Glu | Pro | Gln | Ser | Asp | Pro | Ser | Val | Glu | Pro | Pro | Leu | Ser | Gln |
|---|---|---|---|---|---|---|---|---|---|---|---|---|---|---|---|
| 1 | | | | 5 | | | | | 10 | | | | | 15 | |
| Glu | Thr | Phe | Ser | Asp | Leu | Trp | Lys | Leu | Leu | Pro | Glu | Asn | Asn | Val | Leu |
| | | | 20 | | | | 25 | | | | | 30 | | | |
| Ser | Pro | Leu | Pro | Ser | Gln | Ala | Met | Asp | Asp | Leu | Met | Leu | Ser | Pro | Asp |
| | | | 35 | | | | 40 | | | | | 45 | | | |
| Asp | Ile | Glu | Gln | Trp | Phe | Thr | Glu | Asp | Pro | Gly | Pro | Asp | Glu | Ala | Pro |
| | 50 | | | | | 55 | | | | 60 | | | | | |
| Arg | Met | Pro | Glu | Ala | Ala | Pro | Pro | Val | Ala | Pro | Ala | Pro | Ala | Ala | Pro |
| 65 | | | | | 70 | | | | | 75 | | | | | 80 |
| Thr | Pro | Ala | Ala | Pro | Ala | Pro | Ala | Pro | Ser | Trp | Pro | Leu | Ser | Ser | Ser |
| | | | | 85 | | | | | 90 | | | | | 95 | |
| Val | Pro | Ser | Gln | Lys | Thr | Tyr | Gln | Gly | Ser | Tyr | Gly | Phe | Arg | Leu | Gly |
| | | | 100 | | | | | 105 | | | | | 110 | | |
| Phe | Leu | His | Ser | Gly | Thr | Ala | Lys | Ser | Val | Thr | Cys | Thr | Tyr | Ser | Pro |
| | | 115 | | | | | 120 | | | | | 125 | | | |
| Ala | Leu | Asn | Lys | Met | Phe | Cys | Gln | Leu | Ala | Lys | Thr | Cys | Pro | Val | Gln |
| | 130 | | | | | 135 | | | | | 140 | | | | |
| Leu | Trp | Val | Asp | Ser | Thr | Pro | Pro | Pro | Gly | Thr | Arg | Val | Arg | Ala | Met |
| 145 | | | | | 150 | | | | | 155 | | | | | 160 |
| Ala | Ile | Tyr | Lys | Gln | Ser | Gln | His | Met | Thr | Glu | Val | Val | Arg | Arg | Cys |
| | | | | 165 | | | | | 170 | | | | | 175 | |
| Pro | His | His | Glu | Arg | Cys | Ser | Asp | Ser | Asp | Gly | Leu | Ala | Pro | Pro | Gln |
| | | | 180 | | | | | 185 | | | | | 190 | | |
| His | Leu | Ile | Arg | Val | Glu | Gly | Asn | Leu | Arg | Val | Glu | Tyr | Leu | Asp | Asp |
| | | 195 | | | | | 200 | | | | | 205 | | | |
| Arg | Asn | Thr | Phe | Arg | His | Ser | Val | Val | Val | Pro | Tyr | Glu | Pro | Pro | Glu |
| | 210 | | | | | 215 | | | | | 220 | | | | |
| Val | Gly | Ser | Asp | Cys | Thr | Thr | Ile | His | Tyr | Asn | Tyr | Met | Cys | Asn | Ser |
| 225 | | | | | 230 | | | | | 235 | | | | | 240 |
| Ser | Cys | Met | Gly | Gly | Met | Asn | Arg | Arg | Pro | Ile | Leu | Thr | Ile | Ile | Thr |
| | | | | 245 | | | | | 250 | | | | | 255 | |
| Leu | Glu | Asp | Ser | Ser | Gly | Asn | Leu | Leu | Gly | Arg | Asn | Ser | Phe | Glu | Val |
| | | | 260 | | | | | 265 | | | | | 270 | | |
| Arg | Val | Cys | Ala | Cys | Pro | Gly | Arg | Asp | Arg | Arg | Thr | Glu | Glu | Glu | Asn |
| | | 275 | | | | | 280 | | | | | 285 | | | |
| Leu | Arg | Lys | Lys | Gly | Glu | Pro | His | His | Glu | Leu | Pro | Pro | Gly | Ser | Thr |
| | 290 | | | | | 295 | | | | | 300 | | | | |
| Lys | Arg | Ala | Leu | Pro | Asn | Asn | Thr | Ser | Ser | Ser | Pro | Gln | Pro | Lys | Lys |
| 305 | | | | | 310 | | | | | 315 | | | | | 320 |
| Lys | Pro | Leu | Asp | Gly | Glu | Tyr | Phe | Thr | Leu | Gln | Ile | Arg | Gly | Arg | Glu |
| | | | | 325 | | | | | 330 | | | | | 335 | |
| Arg | Phe | Glu | Met | Phe | Arg | Glu | Leu | Asn | Glu | Ala | Leu | Glu | Leu | Lys | Asp |
| | | | 340 | | | | | 345 | | | | | 350 | | |

| Ala | Gln | Ala | Gly | Lys | Glu | Pro | Gly | Gly | Ser | Arg | Ala | His | Ser | Ser | His |
|---|---|---|---|---|---|---|---|---|---|---|---|---|---|---|---|
| | | 355 | | | | | 360 | | | | | 365 | | | |

| Leu | Lys | Ser | Lys | Lys | Gly | Gln | Ser | Thr | Ser | Arg | His | Lys | Lys | Leu | Met |
|---|---|---|---|---|---|---|---|---|---|---|---|---|---|---|---|
| | 370 | | | | | 375 | | | | | 380 | | | | |

| Phe | Lys | Thr | Glu | Gly | Pro | Asp | Ser | Asp |
|---|---|---|---|---|---|---|---|---|
| 385 | | | | | 390 | | | |

( 2 ) INFORMATION FOR SEQ ID NO:3:

( i ) SEQUENCE CHARACTERISTICS:
        ( A ) LENGTH: 1824 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 778..1623

( x i ) SEQUENCE DESCRIPTION: SEQ ID NO:3:

```
ATCTTCGGGG ATATAAAGTG CATGAGCATA CATCTTGAAA AAAAAAGATG AAAAATTTCC      60

GACTTTAAAT ACGGAAGATA AATACTCCAA CCTTTTTTTC CAATTCCGAA ATTTTAGTCT     120

TCTTTAAAGA AGTTTCGGCT CGCTGTCTTA CCTTTTAAAA TCTTCTACTT CTTGACAGTA     180

CTTATCTTCT TATATAATAG ATATACAAAA CAAAACAAAA CAAAAACTCA CAACACAGGT     240

TACTCTCCCC CCTAAATTCA AATTTTTTTT GCCCATCAGT TTCACTAGCG AATTATACAA     300

CTCACCAGCC ACACAGCTCA CTCATCTACT TCGCAATCAA AACAAAATAT TTTATTTTAG     360

TTCAGTTTAT TAAGTTATTA TCAGTATCGT ATTAAAAAAT TAAAGATCAT TGAAAAATGG     420

CTTGCTAAAC CGATTATATT TTGTTTTTAA AGTAGATTAT TATTAGAAAA TTATTAAGAG     480

AATTATGTGT TAAATTTATT GAAAGAGAAA ATTTATTTTC CCTTATTAAT TAAAGTCCTT     540

TACTTTTTTT GAAAACTGTC AGTTTTTTGA AGAGTTATTT GTTTGTTAC CAATTGCTAT     600

CATGTACCCG TAGAATTTTA TTCAAGATGT TTCCGTAACG GTTACCTTTC TGTCAAATTA     660

TCCAGGTTTA CTCGCCAATA AAAATTTCCC TATACTATCA TTAATTAAAT CATTATTATT     720

ACTAAAGTTT TGTTTACCAA TTTGTCTGCT CAAGAAAATA AATTAAATAC AAATAAA       777
```

| ATG | TCC | GAA | TAT | CAG | CCA | AGT | TTA | TTT | GCT | TTA | AAT | CCA | ATG | GGT | TTC | 825 |
|---|---|---|---|---|---|---|---|---|---|---|---|---|---|---|---|---|
| Met | Ser | Glu | Tyr | Gln | Pro | Ser | Leu | Phe | Ala | Leu | Asn | Pro | Met | Gly | Phe | |
| 1 | | | | 5 | | | | | 10 | | | | | 15 | | |

| TCA | CCA | TTG | GAT | GGT | TCT | AAA | TCA | ACC | AAC | GAA | AAT | GTA | TCT | GCT | TCC | 873 |
|---|---|---|---|---|---|---|---|---|---|---|---|---|---|---|---|---|
| Ser | Pro | Leu | Asp | Gly | Ser | Lys | Ser | Thr | Asn | Glu | Asn | Val | Ser | Ala | Ser | |
| | | | 20 | | | | | 25 | | | | | 30 | | | |

| ACT | TCT | ACT | GCC | AAA | CCA | ATG | GTT | GGC | CAA | TTG | ATT | TTT | GAT | AAA | TTC | 921 |
|---|---|---|---|---|---|---|---|---|---|---|---|---|---|---|---|---|
| Thr | Ser | Thr | Ala | Lys | Pro | Met | Val | Gly | Gln | Leu | Ile | Phe | Asp | Lys | Phe | |
| | | 35 | | | | | 40 | | | | | 45 | | | | |

| ATC | AAG | ACT | GAA | GAG | GAT | CCA | ATT | ATC | AAA | CAG | GAT | ACC | CCT | TCG | AAC | 969 |
|---|---|---|---|---|---|---|---|---|---|---|---|---|---|---|---|---|
| Ile | Lys | Thr | Glu | Glu | Asp | Pro | Ile | Ile | Lys | Gln | Asp | Thr | Pro | Ser | Asn | |
| | 50 | | | | | 55 | | | | | 60 | | | | | |

| CTT | GAT | TTT | GAT | TTT | GCT | CTT | CCA | CAA | ACG | GCA | ACT | GCA | CCT | GAT | GCC | 1017 |
|---|---|---|---|---|---|---|---|---|---|---|---|---|---|---|---|---|
| Leu | Asp | Phe | Asp | Phe | Ala | Leu | Pro | Gln | Thr | Ala | Thr | Ala | Pro | Asp | Ala | |
| 65 | | | | | 70 | | | | | 75 | | | | | 80 | |

| AAG | ACC | GTT | TTG | CCA | ATT | CCG | GAG | CTA | GAT | GAC | GCT | GTA | GTG | GAA | TCT | 1065 |
|---|---|---|---|---|---|---|---|---|---|---|---|---|---|---|---|---|
| Lys | Thr | Val | Leu | Pro | Ile | Pro | Glu | Leu | Asp | Asp | Ala | Val | Val | Glu | Ser | |
| | | | | 85 | | | | | 90 | | | | | 95 | | |

| TTC | TTT | TCG | TCA | AGC | ACT | GAT | TCA | ACT | CCA | ATG | TTT | GAG | TAT | GAA | AAC | 1113 |
|---|---|---|---|---|---|---|---|---|---|---|---|---|---|---|---|---|
| Phe | Phe | Ser | Ser | Ser | Thr | Asp | Ser | Thr | Pro | Met | Phe | Glu | Tyr | Glu | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| CTA | GAA | GAC | AAC | TCT | AAA | GAA | TGG | ACA | TCC | TTG | TTT | GAC | AAT | GAC | ATT | 1161 |
| Leu | Glu | Asp | Asn | Ser | Lys | Glu | Trp | Thr | Ser | Leu | Phe | Asp | Asn | Asp | Ile | |
| | | | | 115 | | | | 120 | | | | 125 | | | | |
| CCA | GTT | ACC | ACT | GAC | GAT | GTT | TCA | TTG | GCT | GAT | AAG | GCA | ATT | GAA | TCC | 1209 |
| Pro | Val | Thr | Thr | Asp | Asp | Val | Ser | Leu | Ala | Asp | Lys | Ala | Ile | Glu | Ser | |
| | 130 | | | | | 135 | | | | | 140 | | | | | |
| ACT | GAA | GAA | GTT | TCT | CTG | GTA | CCA | TCC | AAT | CTG | GAA | GTC | TCG | ACA | ACT | 1257 |
| Thr | Glu | Glu | Val | Ser | Leu | Val | Pro | Ser | Asn | Leu | Glu | Val | Ser | Thr | Thr | |
| 145 | | | | | 150 | | | | | 155 | | | | | 160 | |
| TCA | TTC | TTA | CCC | ACT | CCT | GTT | CTA | GAA | GAT | GCT | AAA | CTG | ACT | CAA | ACA | 1305 |
| Ser | Phe | Leu | Pro | Thr | Pro | Val | Leu | Glu | Asp | Ala | Lys | Leu | Thr | Gln | Thr | |
| | | | | 165 | | | | | 170 | | | | | 175 | | |
| AGA | AAG | GTT | AAG | AAA | CCA | AAT | TCA | GTC | GTT | AAG | AAG | TCA | CAT | CAT | GTT | 1353 |
| Arg | Lys | Val | Lys | Lys | Pro | Asn | Ser | Val | Val | Lys | Lys | Ser | His | His | Val | |
| | | | 180 | | | | | 185 | | | | | 190 | | | |
| GGA | AAG | GAT | GAC | GAA | TCG | AGA | CTG | GAT | CAT | CTA | GGT | GTT | GTT | GCT | TAC | 1401 |
| Gly | Lys | Asp | Asp | Glu | Ser | Arg | Leu | Asp | His | Leu | Gly | Val | Val | Ala | Tyr | |
| | | 195 | | | | | 200 | | | | | 205 | | | | |
| AAC | CGC | AAA | CAG | CGT | TCG | ATT | CCA | CTT | TCT | CCA | ATT | GTG | CCC | GAA | TCC | 1449 |
| Asn | Arg | Lys | Gln | Arg | Ser | Ile | Pro | Leu | Ser | Pro | Ile | Val | Pro | Glu | Ser | |
| | 210 | | | | | 215 | | | | | 220 | | | | | |
| AGT | GAT | CCT | GCT | GCT | CTA | AAA | CGT | GCT | AGA | AAC | ACT | GAA | GCC | GCC | AGG | 1497 |
| Ser | Asp | Pro | Ala | Ala | Leu | Lys | Arg | Ala | Arg | Asn | Thr | Glu | Ala | Ala | Arg | |
| 225 | | | | | 230 | | | | | 235 | | | | | 240 | |
| CGT | TCT | CGT | GCG | AGA | AAG | TTG | CAA | AGA | ATG | AAA | CAA | CTT | GAA | GAC | AAG | 1545 |
| Arg | Ser | Arg | Ala | Arg | Lys | Leu | Gln | Arg | Met | Lys | Gln | Leu | Glu | Asp | Lys | |
| | | | | 245 | | | | | 250 | | | | | 255 | | |
| GTT | GAA | GAA | TTG | CTT | TCG | AAA | AAT | TAT | CAC | TTG | GAA | AAT | GAG | GTT | GCC | 1593 |
| Val | Glu | Glu | Leu | Leu | Ser | Lys | Asn | Tyr | His | Leu | Glu | Asn | Glu | Val | Ala | |
| | | | | 260 | | | | | 265 | | | | | 270 | | |
| AGA | TTA | AAG | AAA | TTA | GTT | GGC | GAA | CGC | TGATTTCATT | | TACCTTTTAT | | | | | 1640 |
| Arg | Leu | Lys | Lys | Leu | Val | Gly | Glu | Arg | | | | | | | | |
| | | 275 | | | | | 280 | | | | | | | | | |

| | | | | | |
|---|---|---|---|---|---|
| TTTATATTTT | TTATTTCATT | CTCGTGTATA | ACGAAATAGA | TACATTCACT | TAGATAAGAA | 1700 |
| TTTAATCTTT | TTTATGCCAA | TTTTCTTAAG | TAGAATTTTA | CACCACGCAT | TTATAATCTG | 1760 |
| CCGTATGTTC | TGGTATTTAC | TGGTTAGGAA | TAGATAAAAA | AAACACTCAC | GATGGGGGTC | 1820 |
| GAAC | | | | | | 1824 |

( 2 ) INFORMATION FOR SEQ ID NO:4:

( i ) SEQUENCE CHARACTERISTICS:
        ( A ) LENGTH: 281 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Ser | Glu | Tyr | Gln | Pro | Ser | Leu | Phe | Ala | Leu | Asn | Pro | Met | Gly | Phe |
| 1 | | | | 5 | | | | | 10 | | | | | 15 | |
| Ser | Pro | Leu | Asp | Gly | Ser | Lys | Ser | Thr | Asn | Glu | Asn | Val | Ser | Ala | Ser |
| | | | 20 | | | | | 25 | | | | | 30 | | |
| Thr | Ser | Thr | Ala | Lys | Pro | Met | Val | Gly | Gln | Leu | Ile | Phe | Asp | Lys | Phe |
| | | 35 | | | | | 40 | | | | | 45 | | | |
| Ile | Lys | Thr | Glu | Glu | Asp | Pro | Ile | Ile | Lys | Gln | Asp | Thr | Pro | Ser | Asn |
| | 50 | | | | | 55 | | | | | 60 | | | | |
| Leu | Asp | Phe | Asp | Phe | Ala | Leu | Pro | Gln | Thr | Ala | Thr | Ala | Pro | Asp | Ala |
| 65 | | | | | 70 | | | | | 75 | | | | | 80 |
| Lys | Thr | Val | Leu | Pro | Ile | Pro | Glu | Leu | Asp | Asp | Ala | Val | Val | Glu | Ser |

|  |  |  |  |  | 85 |  |  | 90 |  |  |  |  | 95 |  |
|---|---|---|---|---|---|---|---|---|---|---|---|---|---|---|
| Phe | Phe | Ser | Ser<br>100 | Ser | Thr | Asp | Ser | Thr<br>105 | Pro | Met | Phe | Glu<br>110 | Tyr | Glu | Asn |
| Leu | Glu | Asp<br>115 | Asn | Ser | Lys | Glu | Trp<br>120 | Thr | Ser | Leu | Phe | Asp<br>125 | Asn | Asp | Ile |
| Pro | Val<br>130 | Thr | Thr | Asp | Asp | Val<br>135 | Ser | Leu | Ala | Asp | Lys<br>140 | Ala | Ile | Glu | Ser |
| Thr<br>145 | Glu | Glu | Val | Ser | Leu<br>150 | Val | Pro | Ser | Asn | Leu<br>155 | Glu | Val | Ser | Thr | Thr<br>160 |
| Ser | Phe | Leu | Pro | Thr<br>165 | Pro | Val | Leu | Glu | Asp<br>170 | Ala | Lys | Leu | Thr | Gln<br>175 | Thr |
| Arg | Lys | Val | Lys<br>180 | Lys | Pro | Asn | Ser | Val<br>185 | Val | Lys | Lys | Ser | His<br>190 | His | Val |
| Gly | Lys | Asp<br>195 | Asp | Glu | Ser | Arg | Leu<br>200 | Asp | His | Leu | Gly | Val<br>205 | Val | Ala | Tyr |
| Asn | Arg<br>210 | Lys | Gln | Arg | Ser | Ile<br>215 | Pro | Leu | Ser | Pro | Ile<br>220 | Val | Pro | Glu | Ser |
| Ser<br>225 | Asp | Pro | Ala | Ala | Leu<br>230 | Lys | Arg | Ala | Arg | Asn<br>235 | Thr | Glu | Ala | Ala | Arg<br>240 |
| Arg | Ser | Arg | Ala | Arg<br>245 | Lys | Leu | Gln | Arg | Met<br>250 | Lys | Gln | Leu | Glu | Asp<br>255 | Lys |
| Val | Glu | Glu | Leu<br>260 | Leu | Ser | Lys | Asn | Tyr<br>265 | His | Leu | Glu | Asn | Glu<br>270 | Val | Ala |
| Arg | Leu | Lys<br>275 | Lys | Leu | Val | Gly | Glu<br>280 | Arg |  |  |  |  |  |  |  |

( 2 ) INFORMATION FOR SEQ ID NO:5:

( i ) SEQUENCE CHARACTERISTICS:
        ( A ) LENGTH: 1824 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 778..1620

( x i ) SEQUENCE DESCRIPTION: SEQ ID NO:5:

| | | | | | |
|---|---|---|---|---|---|
| ATCTTCGGGG | ATATAAAGTG | CATGAGCATA | CATCTTGAAA | AAAAAGATG | AAAAATTTCC | 60 |
| GACTTTAAAT | ACGGAAGATA | AATACTCCAA | CCTTTTTTTC | CAATTCCGAA | ATTTTAGTCT | 120 |
| TCTTTAAAGA | AGTTTCGGCT | CGCTGTCTTA | CCTTTTAAAA | TCTTCTACTT | CTTGACAGTA | 180 |
| CTTATCTTCT | TATATAATAG | ATATACAAAA | CAAACAAAA | CAAAAACTCA | CAACACAGGT | 240 |
| TACTCTCCCC | CCTAAATTCA | AATTTTTTTT | GCCCATCAGT | TTCACTAGCG | AATTATACAA | 300 |
| CTCACCAGCC | ACACAGCTCA | CTCATCTACT | TCGCAATCAA | AACAAAATAT | TTTATTTTAG | 360 |
| TTCAGTTTAT | TAAGTTATTA | TCAGTATCGT | ATTAAAAAAT | TAAAGATCAT | TGAAAAATGG | 420 |
| CTTGCTAAAC | CGATTATATT | TTGTTTTTAA | AGTAGATTAT | TATTAGAAAA | TTATTAAGAG | 480 |
| AATTATGTGT | TAAATTTATT | GAAAGAGAAA | ATTTATTTTC | CCTTATTAAT | TAAAGTCCTT | 540 |
| TACTTTTTTT | GAAAACTGTC | AGTTTTTTGA | AGAGTTATTT | GTTTTGTTAC | CAATTGCTAT | 600 |
| CATGTACCCG | TAGAATTTTA | TTCAAGATGT | TTCCGTAACG | GTTACCTTTC | TGTCAAATTA | 660 |
| TCCAGGTTTA | CTCGCCAATA | AAAATTTCCC | TATACTATCA | TTAATTAAAT | CATTATTATT | 720 |
| ACTAAAGTTT | TGTTTACCAA | TTTGTCTGCT | CAAGAAAATA | AATTAAATAC | AAATAAA | 777 |

| | | | | | | | | | | | | | | | | |
|---|---|---|---|---|---|---|---|---|---|---|---|---|---|---|---|---|
| ATG | TCC | GAA | TAT | CAG | CCA | AGT | TTA | TTT | GCT | TTA | AAT | CCA | ATG | GGT | TTC | 825 |
| Met | Ser | Glu | Tyr | Gln | Pro | Ser | Leu | Phe | Ala | Leu | Asn | Pro | Met | Gly | Phe | |
| 1 | | | | 5 | | | | | 10 | | | | | 15 | | |
| TCA | CCA | TTG | GAT | GGT | TCT | AAA | TCA | ACC | AAC | GAA | AAT | GTA | TCT | GCT | TCC | 873 |
| Ser | Pro | Leu | Asp | Gly | Ser | Lys | Ser | Thr | Asn | Glu | Asn | Val | Ser | Ala | Ser | |
| | | | | 20 | | | | | 25 | | | | | 30 | | |
| ACT | TCT | ACT | GCC | AAA | CCA | ATG | GTT | GGC | CAA | TTG | ATT | TTT | GAT | AAA | TTC | 921 |
| Thr | Ser | Thr | Ala | Lys | Pro | Met | Val | Gly | Gln | Leu | Ile | Phe | Asp | Lys | Phe | |
| | | 35 | | | | | 40 | | | | | 45 | | | | |
| ATC | AAG | ACT | GAA | GAG | GAT | CCA | ATT | ATC | AAA | CAG | GAT | ACC | CCT | TCG | AAC | 969 |
| Ile | Lys | Thr | Glu | Glu | Asp | Pro | Ile | Ile | Lys | Gln | Asp | Thr | Pro | Ser | Asn | |
| | | 50 | | | | | 55 | | | | | 60 | | | | |
| CTT | GAT | TTT | GAT | TTT | GCT | CTT | CCA | CAA | ACG | GCA | ACT | GCA | CCT | GAT | GCC | 1017 |
| Leu | Asp | Phe | Asp | Phe | Ala | Leu | Pro | Gln | Thr | Ala | Thr | Ala | Pro | Asp | Ala | |
| 65 | | | | | 70 | | | | | 75 | | | | | 80 | |
| AAG | ACC | GTT | TTG | CCA | ATT | CCG | GAG | CTA | GAT | GAC | GCT | GTA | GTG | GAA | TCT | 1065 |
| Lys | Thr | Val | Leu | Pro | Ile | Pro | Glu | Leu | Asp | Asp | Ala | Val | Val | Glu | Ser | |
| | | | | 85 | | | | | 90 | | | | | 95 | | |
| TTC | TTT | TCG | TCA | AGC | ACT | GAT | TCA | ACT | CCA | ATG | TTT | GAG | TAT | GAA | AAC | 1113 |
| Phe | Phe | Ser | Ser | Ser | Thr | Asp | Ser | Thr | Pro | Met | Phe | Glu | Tyr | Glu | Asn | |
| | | | | 100 | | | | | 105 | | | | | 110 | | |
| CTA | GAA | GAC | AAC | TCT | AAA | GAA | TGG | ACA | TCC | TTG | TTT | GAC | AAT | GAC | ATT | 1161 |
| Leu | Glu | Asp | Asn | Ser | Lys | Glu | Trp | Thr | Ser | Leu | Phe | Asp | Asn | Asp | Ile | |
| | | 115 | | | | | 120 | | | | | 125 | | | | |
| CCA | GTT | ACC | ACT | GAC | GAT | GTT | TCA | TTG | GCT | GAT | AAG | GCA | ATT | GAA | TCC | 1209 |
| Pro | Val | Thr | Thr | Asp | Asp | Val | Ser | Leu | Ala | Asp | Lys | Ala | Ile | Glu | Ser | |
| | | 130 | | | | | 135 | | | | | 140 | | | | |
| ACT | GAA | GAA | GTT | TCT | CTG | GTA | CCA | TCC | AAT | CTG | GAA | GTC | TCG | ACA | ACT | 1257 |
| Thr | Glu | Glu | Val | Ser | Leu | Val | Pro | Ser | Asn | Leu | Glu | Val | Ser | Thr | Thr | |
| 145 | | | | | 150 | | | | | 155 | | | | | 160 | |
| TCA | TTC | TTA | CCC | ACT | CCT | GTT | CTA | GAA | GAT | GCT | AAA | CTG | ACT | CAA | ACA | 1305 |
| Ser | Phe | Leu | Pro | Thr | Pro | Val | Leu | Glu | Asp | Ala | Lys | Leu | Thr | Gln | Thr | |
| | | | | 165 | | | | | 170 | | | | | 175 | | |
| AGA | AAG | GTT | AAG | AAA | CCA | AAT | TCA | GTC | GTT | AAG | AAG | TCA | CAT | CAT | GTT | 1353 |
| Arg | Lys | Val | Lys | Lys | Pro | Asn | Ser | Val | Val | Lys | Lys | Ser | His | His | Val | |
| | | | 180 | | | | | 185 | | | | | 190 | | | |
| GGA | AAG | GAT | GAC | GAA | TCG | AGA | CTG | GAT | CAT | CTA | GGT | GTT | GTT | GCT | TAC | 1401 |
| Gly | Lys | Asp | Asp | Glu | Ser | Arg | Leu | Asp | His | Leu | Gly | Val | Val | Ala | Tyr | |
| | | | 195 | | | | | 200 | | | | | 205 | | | |
| AAC | CGC | AAA | CAG | CGT | TCG | ATT | CCA | CTT | TCT | CCA | ATT | GTG | CCC | GAA | TCC | 1449 |
| Asn | Arg | Lys | Gln | Arg | Ser | Ile | Pro | Leu | Ser | Pro | Ile | Val | Pro | Glu | Ser | |
| | 210 | | | | | 215 | | | | | 220 | | | | | |
| AGT | GAT | CCT | GCT | GCT | CTA | AAA | CGT | GCT | AGA | AAC | ACT | GAA | GCC | GCC | AGG | 1497 |
| Ser | Asp | Pro | Ala | Ala | Leu | Lys | Arg | Ala | Arg | Asn | Thr | Glu | Ala | Ala | Arg | |
| 225 | | | | | 230 | | | | | 235 | | | | | 240 | |
| CGT | TCT | CGT | GCG | AGA | AAG | TTG | CAA | CGT | CTG | AAA | CAG | ATC | GAA | GAC | AAG | 1545 |
| Arg | Ser | Arg | Ala | Arg | Lys | Leu | Gln | Arg | Leu | Lys | Gln | Ile | Glu | Asp | Lys | |
| | | | | 245 | | | | | 250 | | | | | 255 | | |
| TTA | GAA | GAA | ATC | CTT | TCG | AAG | CTC | TAT | CAC | ATC | GAG | AAT | GAG | TTA | GCG | 1593 |
| Leu | Glu | Glu | Ile | Leu | Ser | Lys | Leu | Tyr | His | Ile | Glu | Asn | Glu | Leu | Ala | |
| | | | 260 | | | | | 265 | | | | | 270 | | | |
| CGC | ATC | AAA | AAA | TTA | TTG | GGT | GAA | CGT | TGATTTCATT | | TACCTTTTAT | | | | | 1640 |
| Arg | Ile | Lys | Lys | Leu | Leu | Gly | Glu | Arg | | | | | | | | |
| | | 275 | | | | | 280 | | | | | | | | | |

| | | |
|---|---|---|
| TTTATATTTT TTATTTCATT CTCGTGTATA ACGAAATAGA TACATTCACT TAGATAAGAA | | 1700 |
| TTTAATCTTT TTTATGCCAA TTTTCTTAAG TAGAATTTTA CACCACGCAT TTATAATCTG | | 1760 |
| CCGTATGTTC TGGTATTTAC TGGTTAGGAA TAGATAAAAA AAACACTCAC GATGGGGGTC | | 1820 |
| GAAC | | 1824 |

( 2 ) INFORMATION FOR SEQ ID NO:6:

( i ) SEQUENCE CHARACTERISTICS:
      ( A ) LENGTH: 281 amino acids
      ( B ) TYPE: amino acid
      ( D ) TOPOLOGY: linear ( i i ) MOLECULE TYPE: protein ( x i ) SEQUENCE DESCRIPTION: SEQ ID NO:6:

```
Met Ser Glu Tyr Gln Pro Ser Leu Phe Ala Leu Asn Pro Met Gly Phe
 1               5                  10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

Ile Lys Thr Glu Glu Asp Pro Ile Ile Lys Gln Asp Thr Pro Ser Asn
    50                  55                  60

Leu Asp Phe Asp Phe Ala Leu Pro Gln Thr Thr Ala Pro Asp Ala
65                  70                  75                  80

Lys Thr Val Leu Pro Ile Pro Glu Leu Asp Asp Ala Val Val Glu Ser
                85                  90                  95

Phe Phe Ser Ser Ser Thr Asp Ser Thr Pro Met Phe Glu Tyr Glu Asn
                100                 105                 110

Leu Glu Asp Asn Ser Lys Glu Trp Thr Ser Leu Phe Asp Asn Asp Ile
            115                 120                 125

Pro Val Thr Thr Asp Asp Val Ser Leu Ala Asp Lys Ala Ile Glu Ser
        130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Lys Lys Ser His His Val
                180                 185                 190

Gly Lys Asp Asp Glu Ser Arg Leu Asp His Leu Gly Val Val Ala Tyr
            195                 200                 205

Asn Arg Lys Gln Arg Ser Ile Pro Leu Ser Pro Ile Val Pro Glu Ser
    210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Leu Lys Gln Ile Glu Asp Lys
                245                 250                 255

Leu Glu Glu Ile Leu Ser Lys Leu Tyr His Ile Glu Asn Glu Leu Ala
            260                 265                 270

Arg Ile Lys Lys Leu Leu Gly Glu Arg
        275                 280
```

( 2 ) INFORMATION FOR SEQ ID NO:7:

( i ) SEQUENCE CHARACTERISTICS:
      ( A ) LENGTH: 3 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:7:

```
Arg Gly Asn
```

1

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:8:

```
Arg  Gly  Gly  Asn  Pro  Glu
 1                 5
```

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:9:

```
Gly  Gly  Asn  Gln  Ala
 1                 5
```

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

GAACATGTCC CAACATGTTG     20

(2) INFORMATION FOR SEQ ID NO:11:

(i) SEQUENCE CHARACTERISTICS:
        (A) LENGTH: 58 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

GGTCAAGTTG GGACACGTCC GGCGTCGGCT GTCGGAGGAG CTAAGTCCTG ACATGTCT     58

(2) INFORMATION FOR SEQ ID NO:12:

(i) SEQUENCE CHARACTERISTICS:
        (A) LENGTH: 234 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..234

(xi) SEQUENCE DESCRIPTION: SEQ ID NO:12:

GCC CCC CCG ACC GAT GTC AGC CTG GGG GAC GAG CTC CAC TTA GAC GGC     48

```
Ala  Pro  Pro  Thr  Asp  Val  Ser  Leu  Gly  Asp  Glu  Leu  His  Leu  Asp  Gly
 1              5                        10                      15

GAG  GAC  GTG  GCG  ATG  GCG  CAT  GCC  GAC  GCG  CTA  GAC  GAT  TTC  GAT  CTG      96
Glu  Asp  Val  Ala  Met  Ala  His  Ala  Asp  Ala  Leu  Asp  Asp  Phe  Asp  Leu
               20                        25                      30

GAC  ATG  TTG  GGG  GAC  GGG  GAT  TCC  CCG  GGG  CCG  GGA  TTT  ACC  CCC  CAC     144
Asp  Met  Leu  Gly  Asp  Gly  Asp  Ser  Pro  Gly  Pro  Gly  Phe  Thr  Pro  His
               35                        40                      45

GAC  TCC  GCC  CCC  TAC  GGC  GCT  CTG  GAT  ATG  GCC  GAC  TTC  GAG  TTT  GAG     192
Asp  Ser  Ala  Pro  Tyr  Gly  Ala  Leu  Asp  Met  Ala  Asp  Phe  Glu  Phe  Glu
          50                        55                       60

CAG  ATG  TTT  ACC  GAT  GCC  CTT  GGA  ATT  GAC  GAG  TAC  GGT  GGG               234
Gln  Met  Phe  Thr  Asp  Ala  Leu  Gly  Ile  Asp  Glu  Tyr  Gly  Gly
 65                       70                         75
```

( 2 ) INFORMATION FOR SEQ ID NO:13:

( i ) SEQUENCE CHARACTERISTICS:
        ( A ) LENGTH: 78 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Ala  Pro  Pro  Thr  Asp  Val  Ser  Leu  Gly  Asp  Glu  Leu  His  Leu  Asp  Gly
 1              5                        10                      15

Glu  Asp  Val  Ala  Met  Ala  His  Ala  Asp  Ala  Leu  Asp  Asp  Phe  Asp  Leu
               20                        25                      30

Asp  Met  Leu  Gly  Asp  Gly  Asp  Ser  Pro  Gly  Pro  Gly  Phe  Thr  Pro  His
               35                        40                      45

Asp  Ser  Ala  Pro  Tyr  Gly  Ala  Leu  Asp  Met  Ala  Asp  Phe  Glu  Phe  Glu
          50                        55                       60

Gln  Met  Phe  Thr  Asp  Ala  Leu  Gly  Ile  Asp  Glu  Tyr  Gly  Gly
 65                       70                         75
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

```
Pro  Lys  Lys  Lys  Arg  Lys  Val
 1              5
```

( 2 ) INFORMATION FOR SEQ ID NO:15:

( i ) SEQUENCE CHARACTERISTICS:
        ( A ) LENGTH: 390 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met  Thr  Ala  Met  Glu  Glu  Ser  Gln  Ser  Asp  Ile  Ser  Leu  Glu  Leu  Pro
 1              5                        10                      15

Leu  Ser  Gln  Glu  Thr  Phe  Ser  Gly  Leu  Trp  Lys  Leu  Leu  Pro  Pro  Glu
               20                        25                      30

Asp  Ile  Leu  Pro  Ser  Pro  His  Cys  Met  Asp  Asp  Leu  Leu  Leu  Pro  Gln
```

|   |   |   | 35  |   |   |   |   | 40  |   |   |   |   | 45  |   |   |
|---|---|---|---|---|---|---|---|---|---|---|---|---|---|---|---|
| Asp | Val 50 | Glu | Glu | Phe | Phe | Glu 55 | Gly | Pro | Ser | Glu | Ala 60 | Leu | Arg | Val | Ser |
| Gly 65 | Ala | Pro | Ala | Ala 70 | Gln | Asp | Pro | Val | Thr 75 | Glu | Thr | Pro | Gly | Pro | Val 80 |
| Ala | Pro | Ala | Pro | Ala 85 | Thr | Pro | Trp | Pro 90 | Leu | Ser | Ser | Phe | Val 95 | Pro | Ser |
| Gln | Lys | Thr | Tyr 100 | Gln | Gly | Asn | Tyr | Gly 105 | Phe | His | Leu | Gly | Phe 110 | Leu | Gln |
| Ser | Gly | Thr 115 | Ala | Lys | Ser | Val | Met 120 | Cys | Thr | Tyr | Ser | Pro 125 | Pro | Leu | Asn |
| Lys | Leu 130 | Phe | Cys | Gln | Leu | Val 135 | Lys | Thr | Cys | Pro | Val 140 | Gln | Leu | Trp | Val |
| Ser 145 | Ala | Thr | Pro | Pro | Ala 150 | Gly | Ser | Arg | Val | Arg 155 | Ala | Met | Ala | Ile | Tyr 160 |
| Lys | Lys | Ser | Gln | His 165 | Met | Thr | Glu | Val | Val 170 | Arg | Arg | Cys | Pro | His 175 | His |
| Glu | Arg | Cys | Ser 180 | Asp | Gly | Asp | Gly | Leu 185 | Ala | Pro | Pro | Gln | His 190 | Leu | Ile |
| Arg | Val | Glu 195 | Gly | Asn | Leu | Tyr | Pro 200 | Glu | Tyr | Leu | Glu | Asp 205 | Arg | Gln | Thr |
| Phe | Arg 210 | His | Ser | Val | Val | Val 215 | Pro | Tyr | Glu | Pro | Pro 220 | Glu | Ala | Gly | Ser |
| Glu 225 | Tyr | Thr | Thr | Ile | His 230 | Tyr | Lys | Tyr | Met | Cys 235 | Asn | Ser | Ser | Cys | Met 240 |
| Gly | Gly | Met | Asn | Arg 245 | Arg | Pro | Ile | Leu | Thr 250 | Ile | Ile | Thr | Leu | Glu 255 | Asp |
| Ser | Ser | Gly | Asn 260 | Leu | Leu | Gly | Arg | Asp 265 | Ser | Phe | Glu | Val | Arg 270 | Val | Cys |
| Ala | Cys | Pro 275 | Gly | Arg | Asp | Arg | Arg 280 | Thr | Glu | Glu | Glu | Asn 285 | Phe | Arg | Lys |
| Lys | Glu 290 | Val | Leu | Cys | Pro | Glu 295 | Leu | Pro | Pro | Gly | Ser 300 | Ala | Lys | Arg | Ala |
| Leu 305 | Pro | Thr | Cys | Thr | Ser 310 | Ala | Ser | Pro | Pro | Gln 315 | Lys | Lys | Lys | Pro | Leu 320 |
| Asp | Gly | Glu | Tyr | Phe 325 | Thr | Leu | Lys | Ile | Arg 330 | Gly | Arg | Lys | Arg | Phe 335 | Glu |
| Met | Phe | Arg | Glu 340 | Leu | Asn | Glu | Ala | Leu 345 | Glu | Leu | Lys | Asp | Ala 350 | His | Ala |
| Thr | Glu | Glu 355 | Ser | Gly | Asp | Ser | Arg 360 | Ala | His | Ser | Ser | Tyr 365 | Leu | Lys | Thr |
| Lys | Lys 370 | Gly | Gln | Ser | Thr | Ser 375 | Arg | His | Lys | Lys | Thr 380 | Met | Val | Lys | Lys |
| Val 385 | Gly | Pro | Asp | Ser | Asp 390 |   |   |   |   |   |   |   |   |   |   |

(2) INFORMATION FOR SEQ ID NO:16:

(i) SEQUENCE CHARACTERISTICS:
  (A) LENGTH: 26 base pairs
  (B) TYPE: nucleic acid
  (C) STRANDEDNESS: double
  (D) TOPOLOGY: linear (ii) MOLECULE TYPE: DNA (genomic)

(xi) SEQUENCE DESCRIPTION: SEQ ID NO:16:

CCCGAACATG TCCCAACATG TTGGGG 26

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

TCGAGCATGT TCGAGCATGT TCGAGCATGT 30

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

CCGGGCATGT CCGGGCATGT CCGGGCATGT 30

(2) INFORMATION FOR SEQ ID NO:19:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

TATGGGCATG TCCTATATAT ATGCGTATAT ATATGGGCAT GTCCTAT 47

(2) INFORMATION FOR SEQ ID NO:20:

(i) SEQUENCE CHARACTERISTICS:
        (A) LENGTH: 1215 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:20:

GAATTCAACC AGCAGCCTCC CGCGACCATG GAGGAGCCGC AGTCAGATCC TAGCGTCGAG 60

CCCCCTCTGA GTCAGGAAAC ATTTTCAGAC CTATGGAAAC TACTTCCTGA AAACAACGTT 120

CTGTCCCCCT TGCCGTCCCA AGCAATGGAT GATTTGATGC TGTCCCCGGA CGATATTGAA 180

CAATGGTTCA CTGAAGACCC AGGTCCAGAT GAAGCTCCCA GAATGCCAGA GGCTGCTCCC 240

CCCGTGGCCC CTGCACCAGC AGCTCCTACA CCGGCCGCCC CTGCACCAGC CCCTCCTGG 300

CCCCTGTCAT CTTCTGTCCC TTCCCAGAAA ACCTACCAGG GCAGCTACGG TTTCCGTCTG 360

GGCTTCTTGC ATTCTGGGAC AGCCAAGTCT GTGACTTGCA CGTACTCCCC TGCCCTCAAC 420

AAGATGTTTT GCCAACTGGC GAAGACCTGC CCTGTGCAGC TGTGGGTTGA TTCCACACCC 480

CCGCCCGGCA CCCGCGTCCG CGCCATGGCC ATCTACAAGC AGTCACAGCA CATGACGGAG 540

GTTGTGAGGC GCTGCCCCCA CCATGAGCGC TGCTCAGATA GCGATGGTCT GGCCCCTCCT 600

| | | | | | |
|---|---|---|---|---|---|
| CAGCATCTTA | TCCGAGTGGA | AGGAAATTTG | CGTGTGGAGT | ATTTGGATGA | CAGAAACACT 660 |
| TTTCGACATA | GTGTGGTGGT | ACCCTATGAG | CCGCCTGAGG | TTGGCTCTGA | CTGTACCACC 720 |
| ATCCACTACA | ACTACATGTG | TAACAGTTCC | TGCATGGGCG | GCATGAACCG | GAGGCCCATC 780 |
| CTCACCATCA | TCACACTGGA | AGACTCCAGT | GGTAATCTAC | TGGGACGGAA | CAGCTTTGAG 840 |
| GTGCGTGTTT | GTGCCTGTCC | TGGGAGAGAC | CGGCGCACAG | AGGAAGAGAA | TCTCCGCAAG 900 |
| AAAGGGGAGC | CTCACCACGA | GCTCCCCCA | GGGAGCACTA | AGCGAGCACT | GCCCAACAAC 960 |
| ACCAGCTCCT | CTCCCCAGCC | AAAGAAGAAA | CCACTGGATG | GAGAATATTT | CACCCTTCAG 1020 |
| ATCCGCGGGC | GTGAGCGCTT | CGAAATGTTC | CGAGAGCTGA | ATGAGGCCTT | GGAACTCAAG 1080 |
| GATGCCCAGG | CTGGGAAGGA | GCCAGGGGGG | AGCAGGGCTC | ACTCCAGCCA | CCTGAAGTCC 1140 |
| AAAAGGGTC | AGTCTACCTC | CCGCCATAAA | AAACTCATGT | TCAAGACAGA | AGGGCCTGAC 1200 |
| TCAGACTGAG | TCGAC | | | | 1215 |

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GCAGAGGAGC AAAAGCTTGA AGACAAGGTT 30

( 2 ) INFORMATION FOR SEQ ID NO:22:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

CTTTAATCAA CCGCTTGCGA CTCAGCTGGA CTTC 34

( 2 ) INFORMATION FOR SEQ ID NO:23:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

ATGAGGCCTT GGAAGACAAG GTTGAAGAAT TG 32

( 2 ) INFORMATION FOR SEQ ID NO:24:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GGGCGTC 7

(2) INFORMATION FOR SEQ ID NO:25:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GACGCCCGC 9

(2) INFORMATION FOR SEQ ID NO:26:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

CGAAATGTTC CGAGAGCGAA TGAAAC 26

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

GTTTCATTCG CTCTCGGAAC ATTT 24

(2) INFORMATION FOR SEQ ID NO:28:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TATCCGCGGT AATCGTCTGA AACAGATCGA AGACAAGTTA GAAGAAATCC TTTCGAAGCT 60

CTATCACATC GAG 73

(2) INFORMATION FOR SEQ ID NO:29:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GCTTCGAGAT AGTGTAGCTC TTACTCAATC GCGCGTAGTT TTTAATAAC CCACTTGCAA 60

CTCAGCTGTT T                                                                                        71

( 2 ) INFORMATION FOR SEQ ID NO:30:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

TTCTCCGCGG AGTGGTTTCT TCTTTGGCTG                                                                    30

( 2 ) INFORMATION FOR SEQ ID NO:31:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

TATCCGCGGT GGAAATCCTG AACTGAAACA GATCGAAGAC AAG                                                     43

( 2 ) INFORMATION FOR SEQ ID NO:32:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

Gly Asn Pro Glu
1

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

GTCATCGATG CGTTCGCCAA CTAATTTCTT                                                                    30

( 2 ) INFORMATION FOR SEQ ID NO:34:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

ATGAGGCCTT GGAACTCATC GATGCCCAGG CTGGG                                                              35

( 2 ) INFORMATION FOR SEQ ID NO:35:

( i ) SEQUENCE CHARACTERISTICS:
  ( A ) LENGTH: 40 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:35:

TTTGTCGACT CAATCGATAC GTTCACCCAA TAATTTTTG    40

( 2 ) INFORMATION FOR SEQ ID NO:36:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:36:

GAGAGCCCCA GTTACCATAA CTACTCT    27

( 2 ) INFORMATION FOR SEQ ID NO:37:

( i ) SEQUENCE CHARACTERISTICS:
  ( A ) LENGTH: 30 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:37:

ATCACGTGAT ATCACGTGAT ATCACGTGAT    30